US 6,617,330 B2

(12) United States Patent
Walter

(10) Patent No.: US 6,617,330 B2
(45) Date of Patent: Sep. 9, 2003

(54) PYRIMIDIN-4-ENAMINE AS FUNGICIDE

(75) Inventor: Harald Walter, Rodersdorf (CH)

(73) Assignee: Syngenta Participations AG (CH)

( * ) Notice: Subject to any disclaimer, the term of this patent is extended or adjusted under 35 U.S.C. 154(b) by 0 days.

(21) Appl. No.: 09/849,931

(22) Filed: May 4, 2001

(65) Prior Publication Data

US 2003/0040521 A1 Feb. 27, 2003

Related U.S. Application Data

(63) Continuation of application No. PCT/EP99/08447, filed on Nov. 4, 1999.

(30) Foreign Application Priority Data

Nov. 6, 1998 (GB) .............................................. 9824332
Nov. 13, 1998 (GB) .............................................. 9824906

(51) Int. Cl.[7] .................... A61K 31/519; A61K 31/517; C07D 475/00; C07C 257/00; A01N 43/54
(52) U.S. Cl. ............................... 514/258.1; 514/264.1; 514/265.1; 514/266.4; 544/255; 544/256; 544/257; 544/278; 544/279; 544/280; 544/283; 564/247; 504/222; 504/240; 504/241
(58) Field of Search .......................... 514/258.1, 264.1, 514/265.1, 266.4; 544/255–257, 278–280, 283; 564/247; 504/222, 240, 241

(56) References Cited

U.S. PATENT DOCUMENTS 5,668,154 A  9/1997  Fink et al. .................. 514/338

FOREIGN PATENT DOCUMENTS

| WO | WO 97 33890 A | 9/1997 |
| WO | WO 99 14202 A | 3/1999 |

OTHER PUBLICATIONS

Brown et. al., Chemical Abstracts, 1976, vol. 84, No. 7, Abstract #43969z, p. 487.*
Ovcharova et al., "Synthesis of Purine Derivatives. XXXII. Transformation of 2–R–1,9–dimethyloxanthines" KHIM–FARM. ZH; 1973; vol. 7 (1); pp. 3–7.

Brown et al., "Dimroth Rearrangement. XVIII. Syntheses and Rearrangement of 4–iminoquinazolines and Related Systems" J. Chem. Soc., Perkin Trans. 1; 1975 (21); pp. 2182–2185.

Tomioka et al. "Photochemistry of (2–nitrophenyl)diazomethane Studied by a Matrix Isolation Technique. (Nitrophenyl)carbene to (carboxylphenyl)nitrene Rearrangement by Successive Reduction of Nitro group with Carbenic Center" J. Am. Chem. Soc.; 1992; vol. 114(21); pp. 8045–8053.

Muravich–Aleksandr et al. "Effect of the Substituent at C–2 on the Direction of Electrophilic Attack in Adenines. Methylation and Protonation of 2–(methylthio)–6–aminopurine Derivatives" ZH ORG. KHIM.; 1987; vol. 23 (4); pp. 848–858.

Chemical Abstracts, vol. 61, No. 8, Oct. 12, 1964, Columbus, Ohio, US; Abstract No. 9497d; Ovcharova et al., "Synthesis of 10–alkyl–6–iminopurines".

Chemical Abstracts, vol. 61, No. 8, Oct. 12, 1964, Columbus, Ohio, US; Abstract No. 9497f; Eckstein et al., "Search for New Xanthine Drugs".

* cited by examiner

Primary Examiner—Richard L. Raymond
Assistant Examiner—Tamthom N. Truong
(74) Attorney, Agent, or Firm—Rose M. Allen

(57) ABSTRACT

Novel pyrimidine derivatives of formula I

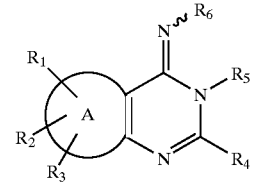

as well as possible isomers and mixtures of isomers thereof.

The novel compounds have plant-protective properties and are suitable for protecting plants against infestations by phytopathogenic microorganisms and insecticidal attack.

15 Claims, No Drawings

PYRIMIDIN-4-ENAMINE AS FUNGICIDE

This is a continuation of PCT/EP99/08447, filed on Nov. 4, 1999.

The present invention relates to novel pyrimidine derivatives of formula I, which have pesticidal activity, in particular fungicidal and insecticidal activity,

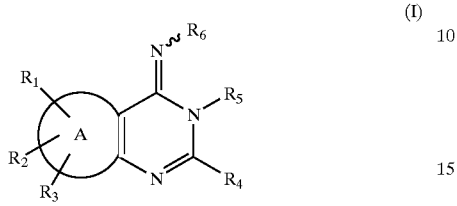

wherein
- A is a 5- or 6-membered ring which may be saturated or unsaturated, aromatic or non-aromatic and which may contain no hetero atoms or 1–3 hetero atoms O, S and/or N, each in the free form or in salt form; with the exception of the imidazolyl ring;
- $R_1$, $R_2$ and $R_3$ are each independently of the other hydrogen; halogen; $C_1$–$C_8$alkyl, $C_2$–$C_8$alkenyl or $C_2$–$C_8$alkinyl which are unsubstituted or mono- to tri-substituted by $C_3$–$C_6$cycloalkyl, halogen, $C_1$–$C_6$alkoxy, $C_1$–$C_6$alkylthio or $C_1$–$C_6$haloalkoxy; O—$C_1$–$C_6$alkyl, O—$C_2$–$C_6$alkenyl, O—$C_2$–$C_6$alkynyl, S—$C_1$–$C_6$alkyl, S—$C_2$–$C_6$alkenyl or S—$C_2$–$C_6$alkynyl, which are unsubstituted or mono- to tri-substituted by $C_3$–$C_6$cycloalkyl, halogen, $C_1$–$C_6$alkoxy or $C_1$–$C_6$haloalkoxy; cyano; nitro; or trimethylsilyl; provided that $R_1$, $R_2$ and $R_3$ are not hydrogen at the same time;
- $R_4$ is $C_1$–$C_8$alkyl, $C_2$–$C_8$alkenyl or $C_2$–$C_8$alkinyl which are unsubstituted or mono- to tri-substituted by $C_3$–$C_6$cycloalkyl, halogen, cyano, nitro, CO—$C_1$–$C_4$alkyl, COO—$C_1$–$C_4$alkyl, CO-aryl, COO-aryl, $C_1$–$C_6$alkylthio, $C_1$–$C_6$alkoxy or $C_1$–$C_6$haloalkoxy; $C_3$–$C_6$cycloalkyl which is unsubstituted or mono- to tri-substituted by $C_1$–$C_6$alkyl, $C_1$–$C_6$haloalkyl, halogen, cyano, $C_1$–$C_6$alkoxy or $C_1$–$C_6$haloalkoxy; phenyl or benzyl, in which the phenyl group is unsubstituted or mono- to pentasubstituted by halogen, cyano, nitro, $C_1$–$C_8$alkyl, $C_2$–$C_8$alkenyl, $C_2$–$C_8$alkinyl, $C_1$–$C_6$alkoxy, $C_1$–$C_6$haloalkoxy or $C_1$–$C_6$haloalkyl; $NHR_7$; $SR_7$ or $OR_7$;
- $R_5$ is $C_1$–$C_8$alkyl, $C_2$–$C_8$alkenyl or $C_2$–$C_8$alkinyl which are unsubstituted or mono- to tri-substituted by $C_3$–$C_6$cycloalkyl, halogen, cyano, nitro, CO—$C_1$–$C_4$alkyl, COO—$C_1$–$C_4$alkyl, CO-aryl, COO-aryl, $C_1$–$C_6$alkoxy, $C_1$–$C_6$alkylthio or $C_1$–$C_6$haloalkoxy; $C_3$–$C_6$cycloalkyl which is unsubstituted or mono- to tri-substituted by $C_1$–$C_6$alkyl, halogen, cyano, $C_1$–$C_6$alkoxy, $C_1$–$C_6$haloalkyl or $C_1$–$C_6$haloalkoxy;
- $R_6$ is hydrogen; $C_1$–$C_8$alkyl, $C_2$–$C_8$alkenyl or $C_2$–$C_8$alkinyl which are unsubstituted or mono- to tri-substituted by $C_3$–$C_6$cycloalkyl, halogen, cyano, nitro, CO—$C_1$–$C_4$alkyl, COO—$C_1$–$C_4$alkyl, CO-aryl, COO-aryl, $C_1$–$C_6$alkoxy, $C_1$–$C_6$alkylthio or $C_1$–$C_6$haloalkoxy; $C_3$–$C_6$cycloalkyl which is unsubstituted or mono- to tri-substituted by $C_1$–$C_6$alkyl, halogen, cyano, $C_1$–$C_6$alkoxy, $C_1$–$C_6$haloalkyl or $C_1$–$C_6$haloalkoxy; O—$C_1$–$C_6$alkyl, O—$C_2$–$C_6$alkenyl, O—$C_2$–$C_6$alkynyl, S—$C_1$–$C_6$alkyl, S—$C_2$–$C_6$alkenyl or S—$C_2$–$C_6$alkynyl, which are unsubstituted or mono- to tri-substituted by $C_3$–$C_6$cycloalkyl, halogen, cyano, $C_1$–$C_6$alkoxy or $C_1$–$C_6$haloalkoxy; aryl or heteroaryl which are unsubstituted or mono- to tri-substituted by halogen, cyano, nitro, $C_1$–$C_6$alkyl, $C_1$–$C_6$haloalkyl, $C_1$–$C_6$alkoxy or $C_1$–$C_6$haloalkoxy; CO—$C_1$–$C_6$alkyl; CO—$C_1$–$C_6$alkyl-O—$C_1$–$C_6$alkyl; CO—$C_1$–$C_6$haloalkyl; CO-heteroaryl; $SO_2$—$C_1$–$C_6$alkyl; $SO_2$-aryl; CO-phenyl or CO—$C_1$–$C_6$alkyl-O-phenyl in which phenyl is unsubstituted or mono- to tri-substituted by halogen, cyano, nitro, $C_1$–$C_6$alkyl, $C_1$–$C_6$haloalkyl, $C_1$–$C_6$alkoxy or $C_1$–$C_6$haloalkoxy; $COOR_8$ wherein $R_8$ is $C_1$–$C_8$alkyl, $C_2$–$C_8$alkenyl, $C_2$–$C_8$alkinyl, $C_3$–$C_4$cycloalkyl or phenyl which is unsubstituted or mono- to tri-substituted by halogen, cyano, nitro, $C_1$–$C_6$alkyl, $C_1$–$C_6$haloalkyl, $C_1$–$C_6$alkoxy or $C_1$–$C_6$haloalkoxy; cyano; nitro; or halogen; and
- $R_7$ is $C_1$–$C_8$alkyl, $C_2$–$C_8$alkenyl or $C_2$–$C_8$alkinyl which are unsubstituted or mono- to tri-substituted by $C_3$–$C_6$cycloalkyl, halogen, cyano, nitro, CO—$C_1$–$C_4$alkyl, COO—$C_1$–$C_4$alkyl, CO-aryl, COO-aryl, $C_1$–$C_6$alkoxy, $C_1$–$C_6$alkylthio or $C_1$–$C_6$haloalkoxy; $C_3$–$C_6$cycloalkyl which is unsubstituted or mono- to tri-substituted by $C_1$–$C_6$alkyl, $C_1$–$C_6$haloalkyl, halogen, cyano, $C_1$–$C_6$alkoxy or $C_1$–$C_6$haloalkoxy; phenyl or benzyl, in which the phenyl group is unsubstituted or mono- to pentasubstituted by halogen, cyano, nitro, $C_1$–$C_8$alkyl, $C_2$–$C_8$alkenyl, $C_2$–$C_8$alkinyl, $C_1$–$C_6$alkoxy, $C_1$–$C_6$haloalkoxy or $C_1$–$C_6$haloalkyl.

The invention also relates to the preparation of these compounds, to agrochemical compositions comprising as active ingredient at least one of these compounds, as well as to the use of the active ingredients or compositions for pest control, in particular as fungicides or insecticides, in agriculture and horticulture.

The compounds I and, optionally, all their isomers may be obtained in the form of their salts. Because the compounds I have at least one basic center they can, for example, form acid addition salts. Said acid addition salts are, for example, formed with mineral acids, typically sulfuric acid, a phosphoric acid or a hydrogen halide, with organic carboxylic acids, typically acetic acid, oxalic acid, malonic acid, maleic acid, fumaric acid or phthalic acid, with hydroxycarboxylic acids, typically ascorbic acid, lactic acid, malic acid, tartaric acid or citric acid, or with benzoic acid, or with organic sulfonic acids, typically methanesulfonic acid or p-toluenesulfonic acid. Together with at least one acidic group, the compounds of formula I can also form salts with bases. Suitable salts with bases are, for example, metal salts, typically alkali metal salts; or alkaline earth metal salts, e.g. sodium salts, potassium salts or magnesium salts, or salts with ammonia or an organic amine, e.g. morpholine, piperidine, pyrrolidine, a mono-, di- or trialkylamine, typically ethylamine, diethylamine, triethylamine or dimethylpropylamine, or a mono-, di- or trihydroxyalkylamine, typically mono-, di- or triethanolamine. Where appropriate, the formation of corresponding internal salts is also possible. Within the scope of this invention, agrochemical acceptable salts are preferred.

Where asymmetrical carbon atoms are present in the compounds of formula I these compounds are in optically active form. Owing to the presence of double bonds, the compounds can be obtained in the [E] and/or [Z] form. Atropisomerism can also occur. The invention relates to the pure isomers, such as enantiomers and diastereomers, as well as to all possible mixtures of isomers, e.g. mixtures of diastereomers, racemates or mixtures of racemates.

The general terms used hereinabove and hereinbelow have the following meanings, unless otherwise defined:

Alkyl groups on their own or as structural element of other groups such as alkoxy are, in accordance with the number of carbon atoms, straight-chain or branched and will typically be methyl, ethyl, n-propyl, isopropyl, n-butyl, sec-butyl, isobutyl, tert-butyl, n-amyl, tert-amyl, 1-hexyl, 3-hexyl, 1-heptyl or 1-octyl.

Alkenyl will be understood as meaning straight-chain or branched alkenyl such as allyl, methallyl, 1-methylvinyl, but-2-en-1-yl, 1-pentenyl, 1-hexenyl, 1-heptenyl or 1-octenyl. Preferred alkenyl radicals contain 3 to 4 carbon atoms in the chain.

Alkynyl can likewise, in accordance with the number of carbon atoms, be straight-chain or branched and is typically propargyl, but-1-yn-1-yl, but-1-yn-3-yl, 1-pentinyl, 1-hexinyl, 1-heptinyl or 1-octinyl. The preferred meaning is propargyl.

Halogen and halo substituents will be understood generally as meaning fluorine, chlorine, bromine or iodine. Fluorine, chlorine or bromine are preferred meanings. Haloalkyl can contain identical or different halogen atoms, typically fluoromethyl, difluoromethyl, difluorochloromethyl, trifluoromethyl, chloromethyl, dichloromethyl, trichloromethyl, 2,2,2-trifluoroethyl, 2-fluoroethyl, 2-chloroethyl, 2,2,2-trichloroethyl, 3,3,3-trifluoropropyl.

Cycloalkyl is, depending on the ring size, cyclopropyl, cyclobutyl, cyclopentyl, cyclohenyl, cycloheptyl or cycooctyl.

Aryl is phenyl, benzyl or naphthyl. Phenyl is preferred. Heteroaryl is pyridinyl, pyrimidinyl, triazinyl, triazolyl, thienyl, thiazolyl, oxazolyl or isoxazolyl.

Preferred compounds are those of formula I, wherein

A is phenyl, cyclohexyl, cyclopentyl, pyridyl, pyrimidinyl, thienyl[3,2-d], thienyl[2,3-d], thienyl[3,4-d], pyrazolyl, thiazolyl or furyl.

Those compounds of formula I are particularly preferred, wherein

A is phenyl;

$R_1$, $R_2$ and $R_3$ are each independently of the other hydrogen; halogen; $C_1$–$C_5$alkyl, $C_2$–$C_5$alkenyl or $C_2$–$C_5$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; provided that $R_1$, $R_2$ and $R_3$ are not all hydrogen at the same time; and at least one of $R_1$, $R_2$ and $R_3$ is halogen;

$R_4$ is $C_1$–$C_5$alkyl, $C_2$–$C_5$alkenyl or $C_2$–$C_5$alkinyl which are unsubstituted or mono to tri-substituted by cyclopropyl, halogen, $C_1$–$C_4$alkoxy, $C_1$–$C_4$alkylthio or $C_1$–$C_4$haloalkoxy;

$C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; $NHR_7$; or $OR_7$;

$R_5$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy;

$C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $COOC_1$–$C_4$alkyl, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; CO—$C_1$–$C_4$alkyl; CO—$C_1$–$C_4$haloalkyl; $SO_2$—$C_1$–$C_4$alkyl; $SO_2$-phenyl; CO—$C_1$–$C_4$alkyl-O—$C_1$–$C_4$alkyl; CO—$C_1$–$C_4$alkyl-O-phenyl; $COOR_8$ wherein $R_8$ is $C_1$–$C_4$alkyl or phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; nitro; or chlorine; and $R_7$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl (subgroup A).

Within the scope of said subgroup A, those compounds of formula I are preferred wherein $R_1$, $R_2$ and $R_3$ are each independently of the other hydrogen; chlorine or bromine; $C_1$–$C_4$alkyl, $C_2$–$C_4$alkenyl or $C_2$–$C_4$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl or O—$C_2$–$C_4$alkynyl, which are unsubstituted or mono- to tri-substituted by cyclopropyl or halogen; provided that $R_1$, $R_2$ and $R_3$ are not hydrogen at the same time; and at least one of $R_1$, $R_2$ and $R_3$ is chlorine or bromine;

$R_4$ is $C_1$–$C_4$alkyl, $C_2$–$C_4$alkenyl or $C_2$–$C_4$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; $NHR_7$; or $OR_7$;

$R_5$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; or nitro; and $R_7$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl (subgroup A1).

Another group of compounds of formula I are preferred, wherein

A is pyridinyl;

$R_1$, $R_2$ and $R_3$ are each independently of the other hydrogen; halogen; $C_1$–$C_5$alkyl, $C_2$–$C_5$alkenyl or $C_2$–$C_5$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; provided that $R_1$, $R_2$ and $R_3$ are not all hydrogen at the same time; and at least one of $R_1$, $R_2$ and $R_3$ is halogen;

$R_4$ is $C_1$–$C_5$alkyl, $C_2$–$C_5$alkenyl or $C_2$–$C_5$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; NHR$_7$; or OR$_7$;

$R_5$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, COOC$_1$–$C_4$alkyl, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; CO—$C_1$–$C_4$alkyl; CO—$C_1$–$C_4$haloalkyl; SO$_2$—$C_1$–$C_4$alkyl; SO$_2$-phenyl; CO—$C_1$–$C_4$alkyl-O—$C_1$–$C_4$alkyl; CO—$C_1$–$C_4$alkyl-O-phenyl; COOR$_8$ wherein R$_8$ is $C_1$–$C_4$alkyl or phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; nitro; or chlorine; and $R_7$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl (subgroup B).

Within the scope of subgroup B, those compounds of formula I are particularly preferred wherein $R_1$, $R_2$ and $R_3$ are each independently of the other hydrogen; chlorine or bromine; $C_1$–$C_4$alkyl, $C_2$–$C_4$alkenyl or $C_2$–$C_4$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl or O—$C_2$–$C_4$alkynyl, which are unsubstituted or mono- to tri-substituted by cyclopropyl or halogen; provided that $R_1$, $R_2$ and $R_3$ are not hydrogen at the same time; and at least one of $R_1$, $R_2$ and $R_3$ is chlorine or bromine;

$R_4$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; NHR$_7$; or OR$_7$;

$R_5$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano or nitro; and $R_7$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl (subgroup B1).

A special group of compounds of formula I are preferred, wherein

A is thienyl[2,3-d];

$R_1$ and $R_2$ are each independently of the other hydrogen; halogen; $C_1$–$C_5$alkyl, $C_2$–$C_5$alkenyl or $C_2$–$C_5$ alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; provided that $R_1$ and $R_2$ are not all hydrogen at the same time; and at least one of $R_1$ and $R_2$ is halogen;

$R_4$ is $C_1$–$C_5$alkyl, $C_2$–$C_5$alkenyl or $C_2$–$C_5$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; $NHR_7$; or $OR_7$;

$R_5$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $COOC_1$–$C_4$alkyl, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; CO—$C_1$–$C_4$alkyl; CO—$C_1$–$C_4$haloalkyl; $SO_2$—$C_1$–$C_4$alkyl; $SO_2$-phenyl; CO—$C_1$–$C_4$alkyl-O—$C_1$–$C_4$alkyl; CO—$C_1$–$C_4$alkyl-O-phenyl; $COOR_8$ wherein $R_8$ is $C_1$–$C_4$alkyl or phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; nitro; or chlorine; and $R_7$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl (subgroup C).

Within the scope of subgroup C, those compounds of formula I are preferred wherein $R_1$ and $R_2$ are each independently of the other hydrogen; chlorine or bromine; $C_1$–$C_4$alkyl, $C_2$–$C_4$alkenyl or $C_2$–$C_4$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl or O—$C_2$–$C_4$alkynyl, which are unsubstituted or mono- to tri-substituted by cyclopropyl or halogen; provided that $R_1$ and $R_2$ are not hydrogen at the same time; and at least one of $R_1$ and $R_2$ is chlorine or bromine;

$R_4$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; $NHR_7$; or $OR_7$;

$R_5$ is $C_1$–$C_4$alkyl, $C_2$–$C_4$alkenyl or $C_2$–$C_4$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; or nitro; and $R_7$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl (subgroup C1).

A group of compounds of formula I are preferred, wherein

A is thienyl[3,2-d];

$R_1$ and $R_2$ are each independently of the other hydrogen; halogen; $C_1$–$C_5$alkyl, $C_2$–$C_5$alkenyl or $C_2$–$C_5$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; provided that $R_1$ and $R_2$ are not all hydrogen at the same time; and at least one of $R_1$ and $R_2$ is halogen;

$R_4$ is $C_1$–$C_5$alkyl, $C_2$–$C_5$alkenyl or $C_2$–$C_5$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; $NHR_7$; or $OR_7$;

$R_5$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, COOC$_1$–$C_4$alkyl, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; CO—$C_1$–$C_4$alkyl; CO—$C_1$–$C_4$haloalkoxy; SO$_2$—$C_1$–$C_4$alkyl; SO$_2$-phenyl; CO—$C_1$–$C_4$alkyl-O—$C_1$–$C_4$alkyl; CO—$C_1$–$C_4$alkyl-O-phenyl; COOR$_8$ wherein R$_8$ is $C_1$–$C_4$alkyl or phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; nitro; or chlorine; and $R_7$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl (subgroup D).

Within the scope of subgroup D, those compounds of formula I are preferred wherein $R_1$ and $R_2$ are each independently of the other hydrogen; chlorine or bromine; $C_1$–$C_4$alkyl, $C_2$–$C_4$alkenyl or $C_2$–$C_4$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl or O—$C_2$–$C_4$alkynyl, which are unsubstituted or mono- to tri-substituted by cyclopropyl or halogen; provided that $R_1$ and $R_2$ are not hydrogen at the same time; and at least one of $R_1$ and $R_2$ is chlorine or bromine;

$R_4$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; NHR$_7$; or OR$_7$;

$R_5$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_{-C4}$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; or nitro; and $R_7$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl (subgroup D1).

The most preferred compounds of the invention disclosed herein are the following ones:
(6-bromo-2-propoxy-3-propyl-3H-quinazolin-4-ylidene) methylamine (cmpd.no. 1.83)
(6-chloro-2-propoxy-3-propyl-3H-quinazolin-4-ylidene) methylamine (cmpd.no. 1.74)
(6-bromo-2-butyl-3-propyl-3H-thieno[2,3-d]pyrimidine-4-ylidene)methylamine (cmpd.no. 4.36)
(6-bromo-2-butyl-3-butyl-3H-thieno[2,3-d]pyrimidine-4-ylidene)methylamine (cmpd.no. 4.37)
(6-chloro-2-propoxy-3-propyl-3H-thieno[2,3-d]pyrimidine-4-ylidene)methylamine (cmpd.no. 4.29)
(6-chloro-2-butyl-3-butyl-3H-thieno[2,3-d]pyrimidine-4-ylidene)carbamic acid methylester (cmpd.no. 4.119)
(6-chloro-2-propoxy-3-propyl-3H-thieno[2,3-d]pyrimidine-4-ylidene)carbamic acid methylester (cmpd.no. 4.120)
N-(6-chloro-2-propoxy-3-propyl-3H-thieno[2,3-d]pyrimidine-4-ylidene)acetamide (cmpd.no. 4.137)
N-(6-chloro-2-butyl-3-propyl-3H-thieno[2,3-d]pyrimidine-4-ylidene)acetamide (cmpd.no. 4.139).

The compounds of formula I can be prepared as follows:

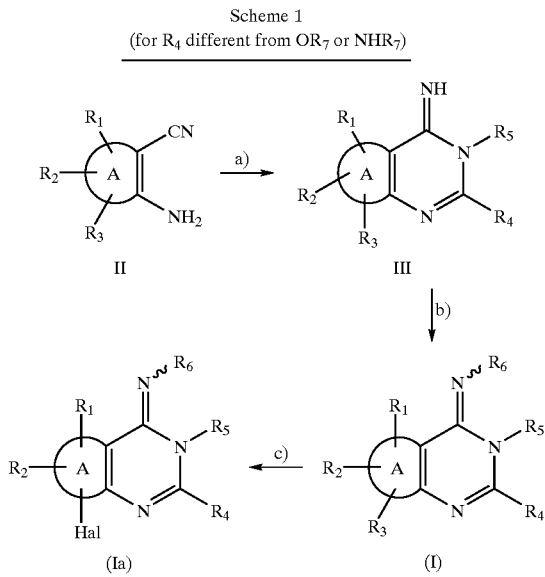

Scheme 1
(for $R_4$ different from OR$_7$ or NHR$_7$)

The compounds of formula I are prepared starting from an 1,2-amino-cyano compound of formula II. The cyclization (step a) in scheme 1) is conveniently carried out in the presence of POCl$_3$, POCl$_3$/PCl$_5$ or SOCl$_2$ in the presence of the amide $R_4$CONHR$_5$ in solvents, such as ClCH$_2$CH$_2$Cl, CHCl$_3$, CH$_2$Cl$_2$, benzene, toluene, xylene, hexane, cyclohexane, dioxane, tetrahydrofuran, chlorobenzene or others in the temperature range from 0° C. to reflux temperature by a reaction time of 15 min. to 18 hours. The resulting compounds III react (step b) in scheme 1) with electrophiles R$_6$X such as alkyl-X, alkenyl-X, alkynyl-X, alkyl-SO$_2$Cl, alkylCOCl, ClCOOalkyl, ClCOOaryl, ClCN or BrCN wherein X is a leaving group like Br, I, Cl, OTosylate, or others in the presence of a weak base such as triethylamine, Hünig-base, pyridine, NaHCO$_3$, Na$_2$CO$_3$, K$_2$CO$_3$ or others in solvents such as THF, dioxane, hexane, toluene, DMSO, DMF, dimethylacetamide or others at temperatures between 0° C. and reflux-temperature during 15 min. to 48 hours. The introduction of an halogen into the ring A (step c) in scheme 1) is obtained by treating compounds of formula I with Cl$_2$, Br$_2$, I$_2$, ICl, N-chlorosuccinimide, N-bromosuccinimide, N-iodosuccinimide, SO$_2$Cl$_2$ or others in a solvent like acetic acid, CH$_2$Cl$_2$, tert.butylmethyl ether, tetrahydrofuran, pyridine, alkylated pyridines, quinoline or others at a temperature range of 0° C. to reflux temperature during 15 min. to 24 hours. Another possibility is the use of halogenated compounds of the formula II, when R$_1$, R$_2$ or R$_3$ are halogen ing aminobenzonitrile IV reacts to the compounds of formula V (step a) in scheme 2) as follows: first reacting with thiophosgene in the presence of a base like trialkylamine, NaHCO$_3$, CaCO$_3$, Na$_2$CO$_3$ or others in a solvent such as tetrahydrofurane, CHCl$_3$/water, CH$_2$Cl$_2$, toluene/water or others at temperatures from 0° to reflux during 1 to 48 hours; and second the reaction of the resulting cyanoisothiocyanate with the amine R$_5$NH$_2$ at temperatures of 0° to reflux during 15 min. to 18 hours. The compounds V are then alkylated or benzylated (step b) in scheme 2) with alkyl-I, alkyl-Br or benzyl-I, benzyl-Br, benzyl-Cl in the presence of a base like NaH, KH, NaOH, Na$_2$CO$_3$, K$_2$CO$_3$ or others in a solvent such as benzene, toluene, cyclohexane, chlorbenzene, CHCl$_3$, CH$_2$Cl$_2$, tetrahydrofuran, tert.butyl methyl ether, DMF or others at temperatures from 0° to reflux during 15 min. to 24 hours. The resulting compounds VI react with 1 to 3 equivalents NaOR$_7$ (step c) in scheme 2) in tetrahydrofuran/R$_7$OH or pure R$_7$OH at temperatures from 0° to reflux during 15 min. to 24 hours. The final products

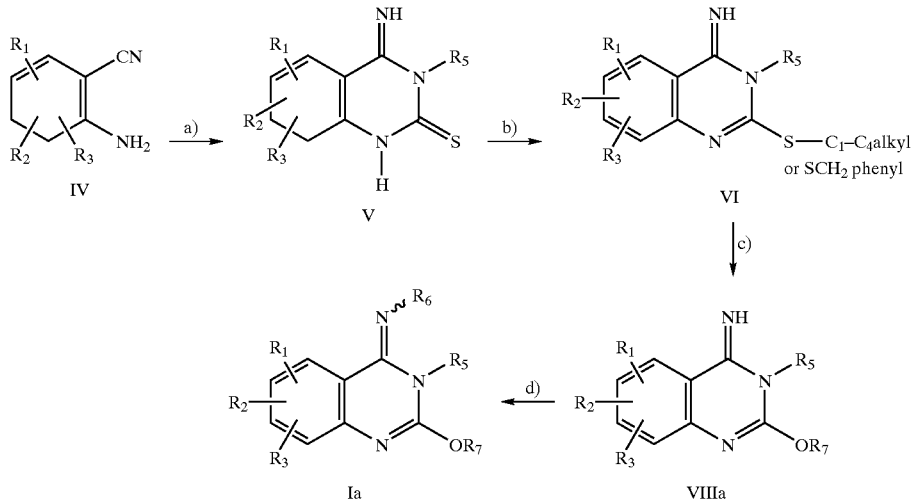

The synthesis of compounds of formula I wherein A is phenyl and R$_4$=OR$_7$ is shown in scheme 2. The corresponding are obtained by step d) in scheme 2 which is equivalent to step b) in scheme 1.

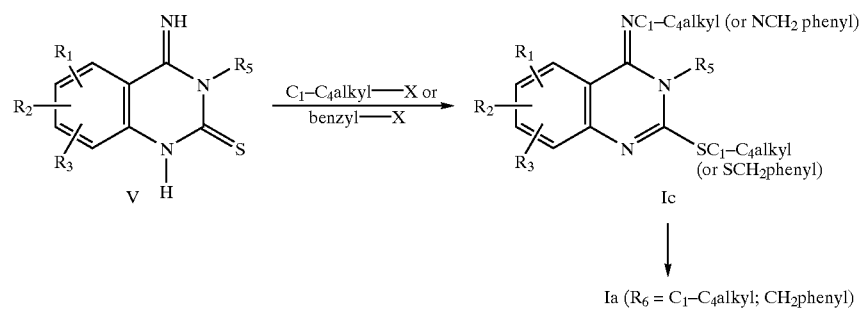

Another synthesis of compounds of formula I wherein A is phenyl, $R_4$=$OR_7$ and $R_6$=$C_1$–$C_4$alkyl or benzyl is shown in scheme 2a. The compounds of formula V react with 2 to 5 equivalents of $C_1$–$C_4$alkyl-X or benzyl-X analogously to step b) in scheme 2 to the alkylated or benzylated compounds of formula Ic. The resulting compounds of formula Ic are then transformed to the compounds of formula Ia analogously step c) in scheme 2. The compounds Ic and Ia can be obtained in the E- and/or Z-form.

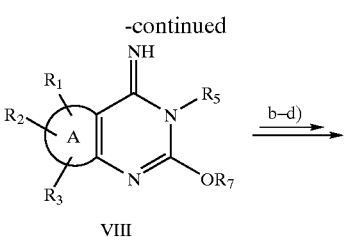

Scheme 3

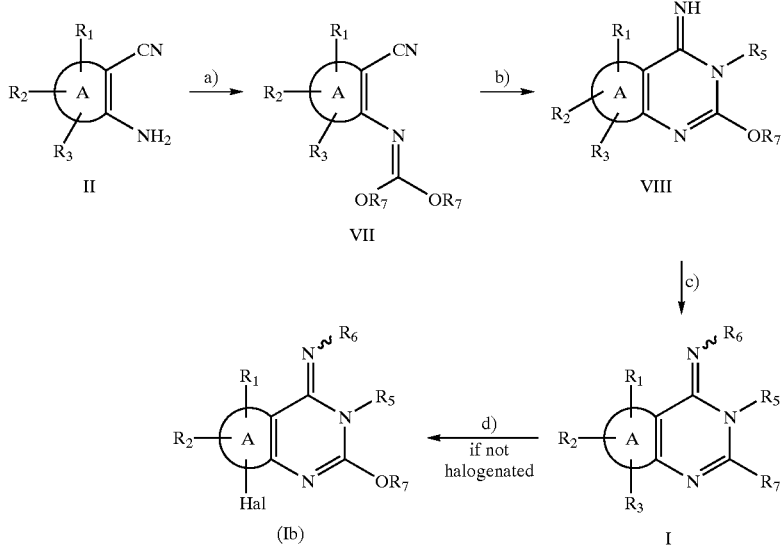

Scheme 3 describes another way to obtain the compounds of formula I. Compounds of formula II react with a tetraalkylorthocarbonate ($(COR_7)_4$, step a) in scheme 3) in the absence or presence of a catalyst like p-TsOH, $CF_3COOH$, $CH_3SO_3H$, HCl, $H_2SO_4$, $HBF_4$, $AlCl_3$, $FeCl_3$, $TiCl_4$ or others in a solvent such as $CHCl_3$, toluene, cyclohexane, tetrahydrofuran or preferred without a solvent at temperatures from 0° to the reflux temperature of the orthocarbonate during 15 min. to 48 hours to the compounds VII. The ring closure is carried out (step b) in scheme 3) in the presence of 1 to 30 equivalents of the amine $R_5NH_2$ where the solvent is either $R_5NH_2$ or tetrahydrofuran, tert.butylmethyl ether, toluene, benzene, dimethylformamide, dimethylsulfoxide or others at temperatures of 0° to reflux during 15 min. to 24 hours. The resulting compounds VIII are then converted to the compounds I by step c in scheme 3 which is equivalent to step b) in scheme 1.

The compounds of the formula I can also be prepared as follows

Schema 4

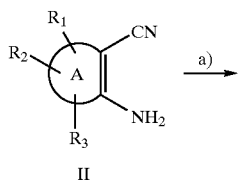

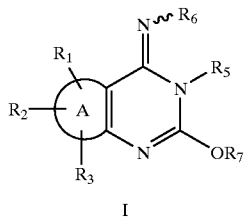

The compound II react with 1 to 3 equivalents of an N-alkylimidocarbonic acid dialkylester like $(R_7O)_2C$=N—$R_5$ (step a in scheme 4) in a solvent such as tetrahydrofuran, tert.butylmethyl ether, toluene, dimethylformamide, dimethylsulfoxide or others in the presence of a base or an acid at temperatures from 0° to reflux during 15 min. to 48 hours to the compounds VIII. The compounds of formula I are obtained by the steps b)–d) in scheme 4 which are analogous to the steps b)–d) in scheme 3.

Scheme 5
The compounds of the formula I can also be prepared as follows

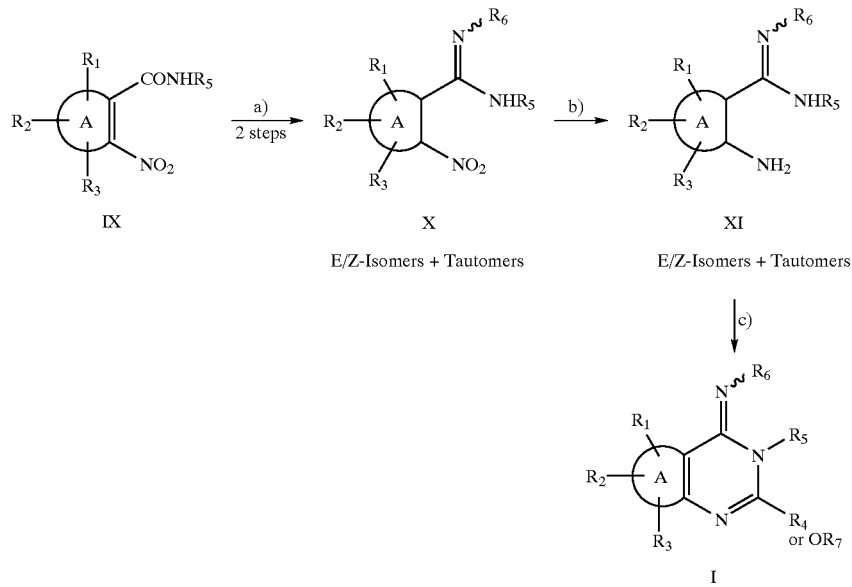

The amides IX known from the literature or, for example in the case of A=phenyl, simple prepared starting from the corresponding benzoic acids, react (step a) in scheme 5) first with $POCl_3$, $POCl_3/PCl_5$, $SOCl_2$, $CCl_4/P(phenyl)_3$, or $CBr_4/P(phenyl)_3$ with or without solvent, preferred without, and then with 1 to 5 equivalents of $R_6NH_2$ in the presence of an additional base like triethylamine, $Na_2CO_3$ or others in a solvent such as tert.butylmethyl ether, tetrahydrofuran, toluene, xylene or others at temperatures from 0° C. to reflux during 1 to 24 hours to the compounds X. Compounds X are hydrogenated (step b) in scheme 5) to compounds XI in the presence of a catalyst like Raney-Ni, Pd or Pt in a solvent such as tetrahydrofuran, alcohols like methanol, ethanol or others at temperatures of 0° C. to reflux during 15 min. to 24 hours. The compounds XI, like the compounds X, can be present in their tautomeric forms XIa or XIb. Compounds of formula XI react with orthocarbonates $C(OR_7)_4$ or orthoesters like alkyl-$C(OR_7)_3$ (step c) in scheme 5) like step a) in scheme 3. Normally mixtures of isomers IA and IB are obtained.

The invention also relates to the intermediates of formula III, V, VI, VII, VIII, X and XI, enclosing the E- and Z-isomers and their tautomeric forms

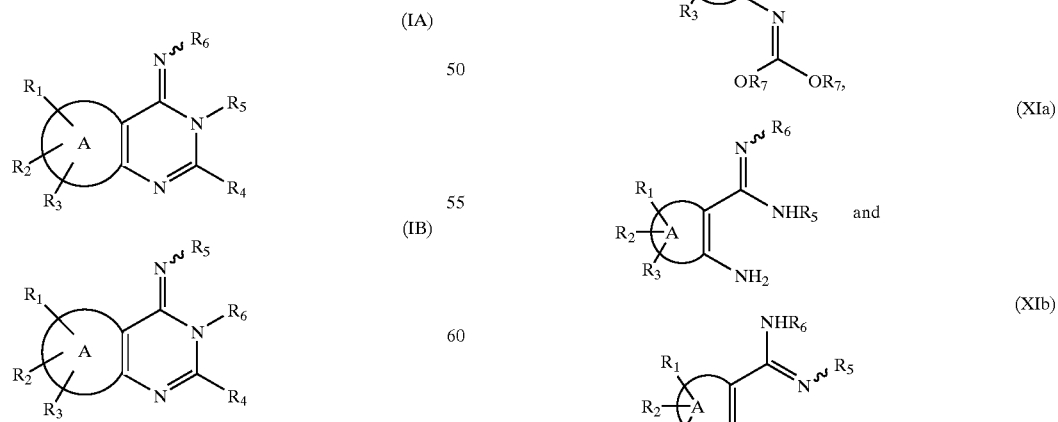

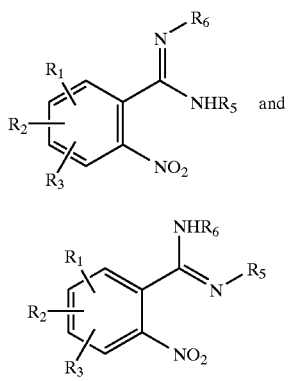

Illustrative examples of such solvents or diluents are: aromatic, aliphatic and alicyclic hydrocarbons and halogenated hydrocarbons, typically benzene, toluene, xylene, chlorobenzene, bromobenzene, petroleum ether, hexane, cyclohexane, dichloromethane, trichloromethane, dichloroethane or trichloroethane; ethers, typically diethyl ether, tert-butylmethyl ether, tetrahydrofuran, or dioxane; ketones, typically acetone or methyl ethyl ketone; alcohols, typically methanol, ethanol, propanol, butanol, ethylene glycol or glycerol; esters, typically ethyl acetate or butyl acetate; amides, typically N,N-dimethylformamide, N,N-dimethylacetamide, N-methyl pyrrolidone or hexamethylphosphoric acid triamide; nitriles, typically acetonitrile; and sulfoxides, typically dimethylsulfoxide. Bases used in excess, such as triethylamine, pyridine, N-methylmorpholine or N,N-diethylaniline, can also be used as solvents or diluents. Suitable bases are, for example, alkali metal hydroxide or alkaline earth metal hydroxide, alkali metal hydride or alkaline earth metal hydride, alkali metal amide or alkaline earth metal amide, alkali metal alkanolate or alkaline earth metal alkanolate, alkali metal carbonate or alkaline earth metal carbonate, alkali metal dialkylamide or alkaline earth metal dialkylamide, or alkali metal alkylsilylamide or alkaline earth metal alkylsilylamide, alkylamines, alkylenediamines, optionally N-alkylated, optionally unsaturated cycloalkylamines, basic heterocycles, ammonium hydroxides and carbocyclic amines. Examples meriting mention are sodium hydroxide, sodium hydride, sodium amide, sodium methanolate, sodium carbonate, potassium tert-butanolate, potassium carbonate, lithium diisopropylamide, potassium bis(trimethylsilyl)amide, calcium hydride, triethylamine, triethylenediamine, cyclohexylamine, N-cyclohexyl-N,N-dimethylamine, N,N-diethylaniline, pyridine, 4-(N,N-dimethylamino)pyridine, N-methylmorpholine, benzyltrimethylammonium hydroxide, and 1,8-diazabicyclo[5.4.0]undec-5-ene (DBU).

The present invention also relates to novel nitrobenzamidine derivatives of formula X (when A is phenyl tautomers Xa and Xb) as intermediates, in their tautomeric forms

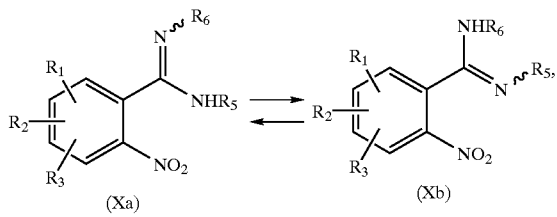

and their possible isomers and mixtures of isomers and wherein $R_1$, $R_2$, $R_3$, $R_5$ and $R_6$ have the meaning given for the compounds of formula I and wherein $R_5$ is also hydrogen.

Formula X is understood to comprise the two tautomeric forms Xa and Xb.

The compounds X and their tautomers (Xa and Xb) or/and their E/Z-isomers may be obtained in the form of their salts. Because the compounds X (Xa and Xb) have at least one basic center they can, for example, form acid addition salts. Said acid addition salts are, for example, formed with mineral acids, typically sulfuric acid, a phosphoric acid or a hydrogen halide, with organic carboxylic acids, typically acetic acid, oxalic acid, malonic acid, maleic acid, fumaric acid or phthalic acid, with hydroxycarboxylic acids, typically ascorbic acid, lactic acid, malic acid, tartaric acid or citric acid, or with benzoic acid, or with organic sulfonic acids, typically methanesulfonic acid or p-toluenesulfonic acid. Together with at least one acidic group, the compounds of formula X (Xa and Xb) can also form salts with bases. Suitable salts with bases are, for example, metal salts, typically alkali metal salts or alkaline earth metal salts, e.g. sodium salts, potassium salts or magnesium salts, or salts with ammonia or an organic amine, e.g. morpholine, piperidine, pyrrolidine, a mono-, di- or trialkylamine, typically ethylamine, diethylamine, triethylamine or dimethylpropylamine, or a mono-, di- or trihydroxyalkylamine, typically mono-, di- or triethanolamine. Where appropriate, the formation of corresponding internal salts is also possible. Within the scope of this invention, agrochemical acceptable salts are preferred.

Where asymmetrical carbon atoms are present in the compounds of formula X (Xa and Xb), these compounds are in optically active form. Owing to the presence of double bonds, the compounds can be obtained in the [E] and/or [Z] form. Atropisomerism can also occur. The invention relates to the pure isomers, such as enantiomers and diastereomers, as well as to all possible mixtures of isomers, e.g. mixtures of diastereomers, racemates or mixtures of racemates.

Preferred compounds are those of formula X, wherein $R_1$, $R_2$ and $R_3$ are each independently of the other hydrogen or halogen; and $R_6$ and $R_5$ are each independently of the other hydrogen; halogen; $C_1$–$C_5$alkyl unsubstituted or substituted by $C_3$–$C_4$cycloalkyl; $C_2$–$C_5$alkenyl; $C_2$–$C_5$alkynyl; $C_3$–$C_4$cycloalkyl; $C_1$–$C_5$alkoxy; $C_1$–$C_5$haloalkyl; or $C_1$–$C_4$haloalkoxy (subgroup AA).

Within the scope of said subgroup AA, those compounds of formula X are preferred wherein $R_1$, $R_2$ and $R_3$ are each independently of the other hydrogen, chlorine, bromine or iodine;

$R_6$ is $C_1$–$C_3$alkyl, $OCH_3$, $CF_3$, $C_3$–$C_5$alkenyl, $C_3$–$C_4$cycloalkyl or $C_3$–$C_5$alkynyl; and $R_5$ is $C_3$–$C_5$alkyl, $C_3$–$C_5$alkenyl, $C_3$–$C_5$alkynyl, $C_3$–$C_4$cycloalkyl or —$CH_2$-cyclopropyl (subgroup BA).

The intermediate compounds of formula X may be prepared as follows:

Scheme 6

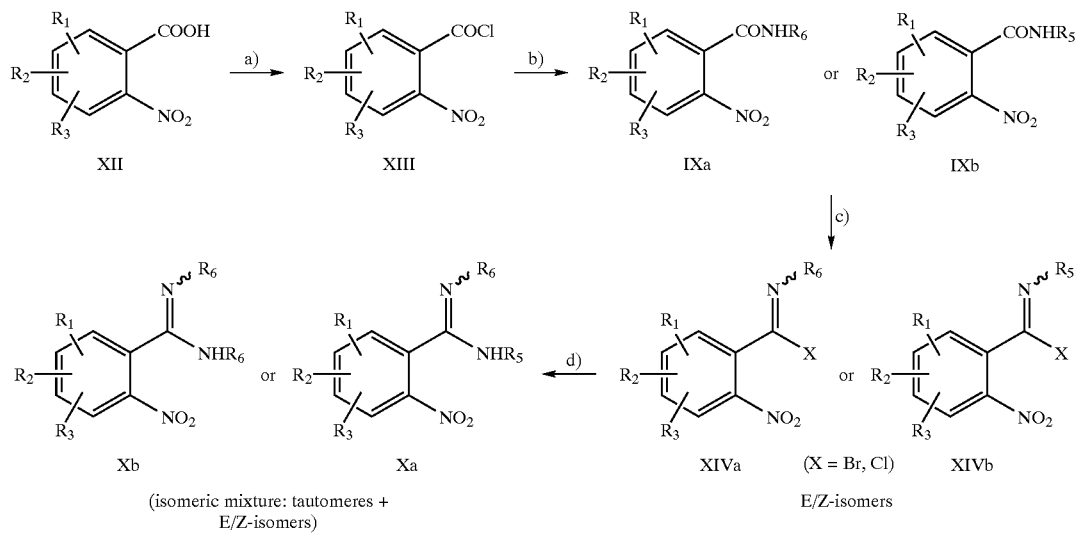

(isomeric mixture: tautomeres + E/Z-isomers)

E/Z-isomers

The compounds of formula X (Xa and Xb) are preferably prepared starting from the corresponding nitrobenzoic acids well known from the literature or easily synthesized by nitration of the known halobenzoic acids. The preparation of the nitrobenzoic acid chloride XIII (step a) in scheme 6) is conveniently carried out by the reaction of XII with $POCl_3$, $POCl_3/PCl_5$ or $SOCl_2$, in solvents, such as $ClCH_2CH_2Cl$, $CHCl_3$, $CH_2Cl_2$, toluene, hexane, cyclohexane or others, or without solvent in the temperature range from 0° C. to reflux temperature during 0.5 to 24 hours, in the absence or presence of a catalyst like trialkylamine or pyridine. The acid chloride XIII is then converted into the corresponding amides IX (IXa or IXb)(step b) in scheme 6) by reaction of XIII with the amine $H_2NR_6$ or the amine $H_2NR_5$ in the presence of additional bases like trialkylamine, pyridine, $Na_2CO_3$, $K_2CO_3$ or the like in a solvent such as ethers (tert.-butylmethylether, tetrahydrofuran), halohydrocarbons ($CH_2Cl_2$, $CHCl_3$), aromatic hydrocarbons (toluene, xylene) or others in the temperature range from 0° C. to reflux temperature during 0.5 to 24 hours. Halogenation of IX (IXa or IXb)(step c) in scheme 6) with $POCl_3$, $POCl_3/PCl_5$, $SOCl_2$, $CCl_4/P(phenyl)_3$ or $CBr_4/P(phenyl)_3$ in the absence or presence of catalyst like weak bases without or in the presence of solvents such as $ClCH_2CH_2Cl$, $CHCl_3$, $CH_2Cl_2$, toluene, hexane, cyclohexane or others, in the temperature range from 0° C. to reflux temperature during 0.5 to 24 hours, yields compounds XIV (XIVa or XIVb). The resulting compounds XIV (XIVa or XIVb) are converted to the nitrobenzamidine products X (Xa or Xb)(step d) in scheme 6) by the reaction of XIV with $H_2NR_5$ or $H_2NR_6$ in solvents such as tetrahydrofuran, dioxane, tert.-butylmethylether, hexane, toluene, cyclohexane, $ClCH_2CH_2Cl$, $CHCl_3$, $CH_2Cl_2$, or others at temperatures between 0° C. and reflux-temperature during 0.5 to 24 hours under possible addition of bases like trialkylamine or pyridine.

Scheme 7

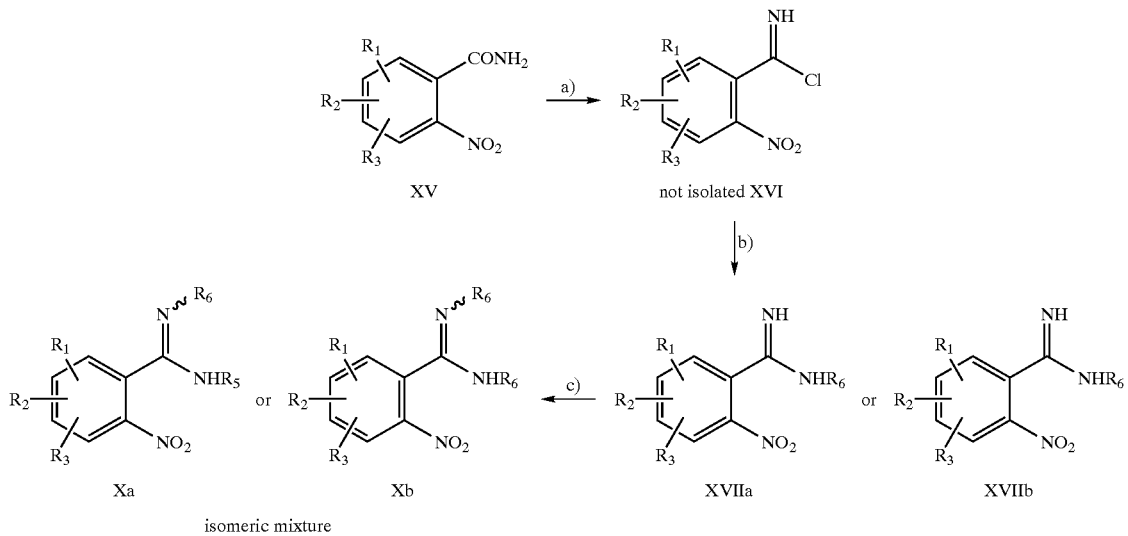

isomeric mixture

The reactions steps a) and b) in scheme 7 corresponds to the reactions steps c) and d) in scheme 6. The reaction of intermediates XVII (step c) in scheme 7) with $R_5X$ or $R_6X$ (X=Br,I), dimethyl- or diethylsulfate, ClCN, BrCN, ClCOOalkyl, NCS, NBS, NIS, alkylCOCl, alkylSO$_2$Cl or others in the presence of a base like triethylamine, pyridine, Na$_2$CO$_3$, K$_2$CO$_3$ or the like in a solvent such tetrahydrofuran, sulfolane, dimethylformamide, dimethylsulfoxide, CHCl$_3$, CH$_2$Cl$_2$, toluene, cyclohexane or others in the temperature range from 0° C. to reflux temperature during 0.5 to 24 hours yields the compounds of formula X (Xa and Xb).

The invention also relates to the intermediate of formula XIV, namely XIVa and XIVb

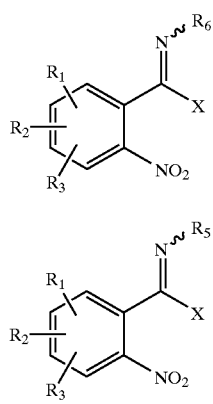

and to the intermediate XVII, namely XVIIa and XVIIb

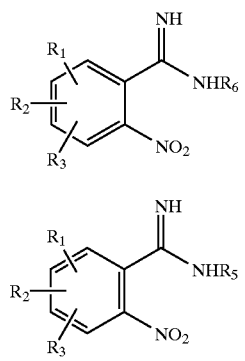

Surprisingly, it has now been found that the novel compounds of formula I have, for practical purposes, a very advantageous spectrum of activities for protecting plants against diseases that are caused by fungi as well as by bacteria and viruses. The compounds of formula I can be used in the agricultural sector and related fields as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic micro-organisms.

The compounds of the formula I according to the invention furthermore are valuable active compounds against insects and pests of the order Acarina such as occur on useful plants and ornamentals in agriculture and in horticulture and in forestry. The compounds of the formula I are particularly suitable for controlling pests in cotton, vegetable, fruit and rice crops, such as spider mites, aphids, butterfly caterpillars and rice cicadas. Spider mites such as *Panonychus ulmi,* aphids such as *Aphids craccivora,* butterfly caterpillars such as those of *Heliothis virescens* and rice cicadas such as *Nilaparvata lugens* or *Nephotettix cincticeps* may chiefly be controlled.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

The compounds I are, for example, effective against the phytopathogenic fungi of the following classes: Fungi imperfecti (e.g. Botrytis, Pyricularia, Heiminthosporium, Fusarium, Septoria, Cercospora and Alternaria) and Basidiomycetes (e.g. Rhizoctonia, Hemileia, Puccinia). Additionally, they are also effective against the Ascomycetes classes (e.g. Venturia and Erysiphe, Podosphaera, Monilinia, Uncinula) and of the Oomycetes classes (e.g. Phytophthora, Pythium, Plasmopara). Furthermore, the novel compounds of formula I are effective against phytopathogenic bacteria and viruses (e.g. against Xanthomonas spp, Pseudomonas spp, *Erwinia amylovora* as well as against the tobacco mosaic virus).

Within the scope of this invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) or plants such as tobacco, nuts, coffee, eggplants, sugar cane, tea, pepper, vines, hops, bananas and natural rubber plants, as well as ornamentals.

The compounds of formula I are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2[(2-trifluoromethyl)-pyrid-6-yloxymethyl]-3-methoxy-acrylate or 2-[{α[(α-methyl-3-trifluoromethyl-benzyl)imino]-oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenylamino-3,5-di-hydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfon-amide (IKF-916), N-(1-cyano-1,2-dimethylpropyl)-2-(2,4-dichlorophenoxy)-propionamide (AC 382042) or iprovalicarb (SZX 722).

Suitable carriers and adjuvants can be solid or liquid and are substances useful in formulation technology, e.g. natural or regenerated mineral substances, solvents, dispersants, wetting agents, tackifiers, thickeners, binders or fertilizers.

A preferred method of applying a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners binding agents or fertilizers. Such carriers are for example described in WO 97/33890.

Further surfactants customarily employed in the art of formulation are known to the expert or can be found in the relevant literature.

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilizers, antifoams, viscosity regulators, binders or tackifiers as well as fertilizers, micronutrient donors or other formulations for obtaining special effects.

The following non-limitative Examples illustrate the above-described invention in more detail. Temperatures are given in degrees Celsius. The following abbreviations are used: Et=ethyl; i-propyl=isopropyl; Me=methyl; m.p.= melting point. "NMR" means nuclear magnetic resonance spectrum. MS=mass spectrum. "%" is percent by weight, unless corresponding concentrations are indicated in other units.

PREPARATION EXAMPLES

Example P-1

5-Chloro-2-nitro-N,N'-dipropylbenzamidine

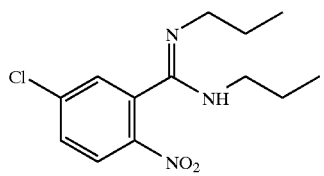

In a sulfonation flask 32.8 g (0.125 mol) 5-chloro-2-nitrobenzoic acid propylamide are dissolved in 74.4 g (0.625 mol) SOCl$_2$ and heated at reflux temperature for 4 hours. Then the excess SOCl$_2$ is removed in a water jet vacuum and the crude imidoylchloride is dissolved in 30 ml of absolute THF. The resulting solution was added dropwise to a stirred solution of 15.4 g (0.26 mol) 1-aminopropane in 30 ml THF. The mixture is stirred for 5 hours at reflux temperature and then the solvent is removed in a water jet vacuum. The residue is taken up in ethylacetate and the organic phase is washed twice with water and saturated sodiumcarbonate solution. After drying of the organic phase, the solvent is removed in a water jet vacuum and the raw material purified by column chromatography over silica gel (eluant: hexane/THF=3:1). Yield: 27.8 g 5-chloro-2-nitro-N,N'-dipropylbenzamidine in the form of brown crystals; m.p. 63–64° C.

Example P-2

2-Amino-5-chloro-N,N'-dipropylbenzamidine

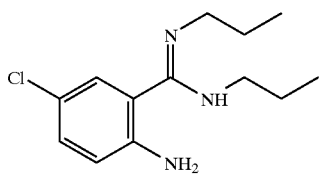

27.4 g (0.097 mol) of 5-chloro-2-nitro-N,N'-dipropylbenzamidine are dissolved in 200 ml of THF and are hydrogenated in the presence of 15 g Ra—Ni/EtOH at room temperature for 5 hours (take up of hydrogen: 94%). Then the catalyst is filtered off and the solvent removed in a water jet vacuum. The residue is purified by column chromatography on silica gel (eluant: hexane/THF 1:1, then THF). Yield: 11.9 g of 2-amino-5-chloro-N,N'-dipropylbenzamidine in the form of a brown oil ($^1$H-NMR (CDCl$_3$);.ppm/multiplicity/number of H's): 0.91/m/6H; 1.56/m/4H; 3.10/m (broad)/4H, 3.75/s(broad)/2H; 6.63/d/1H; 7.02/d/1H; 7.10/dd/1H.

Example P-3

(6-Chloro-2-propoxy-3-propyl-3H-quinazoline-4-ylidene)propylamine

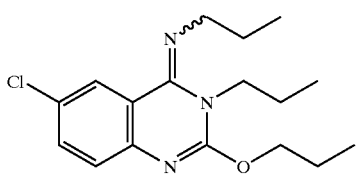

[cmpd. no 1.152]

In a small distillation apparatus 2.5 g (9.8 mmol) of 2-amino-5-chloro-N,N'-dipropylbenzamidine and 3.4 g (13.8 mmol) tetra-n-propylorthocarbonate are heated at 135° C. for 14 hours. Then propanol and excess tetra-n-propylorthocarbonate are distilled off in a water jet vacuum and the residue is purified by column chromatography on silica gel (eluant: hexane/tert.butylmethylether 10:1). Yield: 1.1 g of (6-chloro-2-propoxy-3-propyl-3H-quinazolidine-4-ylidene)propylamine in the form of brownish crystals, m.p. 50–51° C.

Example P-4

2-Butyl-3-propyl-3H-thieno [2,3-d]pyrimidine-4-ylideneamine

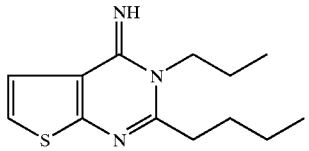

[cmpd. no 4.3]

In a sulfonation flask 11.16 g (0.09 mol) 2-amino-3-cyanothiophene and 1.43 g(0.1 mol) of valeric acid propylamide are dissolved in 150 ml toluene and heated up to 50° C. To this solution 16.9 g (0.11 mol) of POCl$_3$ are added dropwise at a constant temp. of ~50–55° C. After completion of the addition the mixture is stirred at reflux temperature for 1 h. Then toluene is removed in a water jet vacuum, and the residue taken up in ethylacetate. The organic phase is washed several times with a saturated sodiumcarbonate solution and after drying of the organic phase over Na$_2$SO$_4$ the solvent is removed in vacuum. The resulting brown oil (19.4 g) consists of pure 2-butyl-3-propyl-3H-thieno [2,3-d] pyrimidine-4-ylideneamine ($^1$H-NMR-data see table 5).

Example P-5

(2-Butyl-3-propyl-3H-thieno[2,3-d]pyrimidin-4-ylidene)methylamine

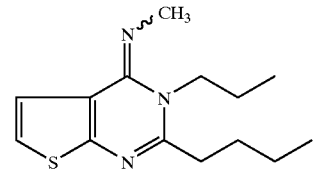

In a sulfonation flask 3.74 g (0.015 mol) 2-butyl-3-propyl-3H-thieno [2,3-d]pyrimidine-4-ylideneamine, 2.84 g (0.03 mol) MeI, 4.15 g (0.03 mol) powdered sodium carbonate and 50 ml abs. DMF are stirred for 4 hours at an internal temperature of 70° C. Then DMF is distilled off in vacuum and the residue taken up in ethylacetate. The organic phase is washed with water and after drying the organic phase over Na$_2$SO$_4$ the solvent is removed in a water jet vacuum. The raw material is purified by column chromatography over silica gel (eluant: hexane/THF 1:1). Yield: 2.7 g of (2-butyl-3-propyl-3H-thieno [2,3-d]pyrimidin-4-ylidene) methylamine in the form of yellow crystals, m.p. 45–47° C.

Example P-6

(2-Butyl-6-chloro-3-propyl-3H-thieno [2,3-d]pyrimidine-4-ylidene)methylamine

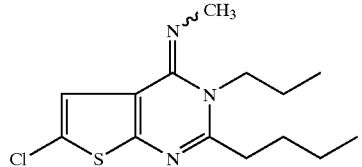

[cmpd. no 4.27]

In a sulfonation flask, 0.92 g (3.5 mmol) (2-butyl-3-propyl-3H-thieno [2,3-d] pyrimidine-4-ylidene)

methylamine are dissolved in 10 ml of absolute pyridine and heated up to 70° C. Then 0.71 g (5.3 mmol) N-chlorosuccinimide are added and the resulting mixture is heated for 1 h at 70° C. After completion of the reaction, pyridine is removed in a water jet vacuum and the residue taken up in ethylacetate. The organic phase is washed several times with water and after drying of the organic phase with Na₂SO₄, the solvent is removed in vacuum. The raw material is purified by column chromatography over silica gel (eluant: hexane/THF 2:1). Yield: 0.95 g of (2-butyl-6-chloro-3-propyl-3H-thieno [2,3-d]pyrimidin-4-ylidene) methylamine in the form of a brown oil ($^1$H-NMR-data see table 5).

Example P-7

3-Cyano-2-(1,1-dipropoxymethylenamino)thiophene

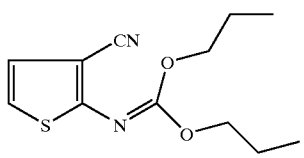

In a small distillation apparatus a mixture of 12.4 g(0.1 mol) 2-amino-3-cyanothiophene and 37.2 g (0.15 mol) tetra-n-propylorthocarbonate is heated for 3 hours at 155° C. n-PrOH, which arises during the reaction is directly distilled out of the reaction flask. After completion of the reaction, excess tetra-n-propylorthocarbonate is distilled off under reduced pressure and the resulting raw material purified by column chromatography over silica gel (eluant: hexane/tert.butylmethyl ether 6:1). Yield: 10.6 g of 3-cyano-2-(1,1-dipropoxymethyleneamino)thiophene in the form of slightly brownish crystals; m.p. 65–67° C.

Example P-8

5-Chloro-3-cyano-2-(1,1-dipropoxymethylenamino)thiophene)

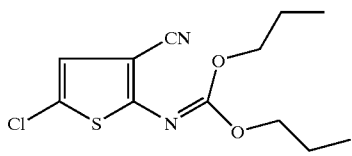

In a sulfonation flask, 3.02 g (0.012 mol) 3-cyano-2-(1,1-dipropoxymethylenamino)thiophene, are added, with stirring to 15 ml of absolute pyridine. The internal temperature is then raised to 60° C. and 1.9 g (0.0144 mol) N-chlorosuccinimide are added in three portions. After stirring for 3 hours at 60° C., the pyridine is removed in a water jet vacuum and the residue taken up in ethylacetate. The organic phase is washed twice with water and after drying, the solvent is removed in a water jet vacuum. The crude product is purified by column chromatography over silica gel (eluant: tert.butylmethylether/hexane 1:6). Yield: 3.5 g of 5-chloro-3-cyano-2-(1,1-dipropoxymethyleneamino)thiophene in the form of brownish crystals, m.p. 55–57° C.

Example P-9

3-Propyl-2-propoxy-3H-thieno [2,3-d]pyrimidine-4-ylideneamine

[cmpd. no 4.5]

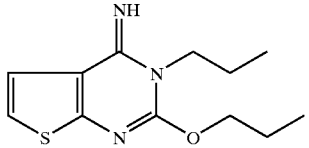

In a sulfonation flask, 5.7 g (0.023 mol) 3-cyano-2-(1,1-dipropoxymethylenamino)thiophene and 35 ml 1-aminopropane are heated at reflux temperature for 5 hours. Then the excess of 1-aminopropane is distilled off and the residue purified by column chromatography over silica gel (eluant: hexane/ethylacetate 1:1). Yield: 5.1 g of 3-propyl-2-propoxy-3H-thieno[2,3-d]pyrimidine-4-ylideneamine in the form of brownish crystals; m.p. 61–63° C.

Example P-10

(3-Propyl-2-propoxy-3H-thieno[2,3-d]pyrimidine-4-ylidene)methylamine

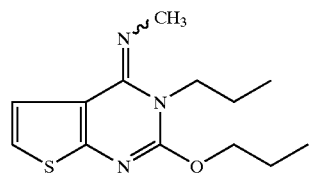

In a sulfonation flask 4.5 g (0.018 mol) 3-propyl-2-propoxy-3H-thieno[2,3-d]pyrimidine-4-ylidene amine, 5.1 g (0.036 mol) CH₃I, 5.0 g (0.036 mol) powdered potassium carbonate and 80 ml of absolute DMF are stirred for 4 hours at an internal temperature of 90–100° C. Then the solvent is distilled off in vacuum, the residue taken up in ethylacetate and the organic phase twice washed with water. After drying the organic phase over Na₂SO₄ the ethylacetate is distilled off in a water jet vacuum and the residue purified by column chromatography over silica gel (eluant: hexane/ethylacetate 1:6). Yield: 4.4 g of (3-propyl-2-propoxy-3H-thieno[2,3-d]pyrimidine-4-ylidene)methylamine in the form of a brown oil.

$^1$H-NMR (CDCl₃; ppm/multiplicity/number of H's): 0.92/t/3H; 1.03/t/3H; 1.63/m/2H; 1.79/m/2H; 3.42/s/3H; 4.01/t/2H; 4.31/t/2H; 6.81/d/1H; 7.59/d/1H.

Example P-11

(6-Bromo-3-propyl-2-propoxy-3H-thieno[2,3-d]pyrimidine-4-ylidene)methylamine

[cmpd. no 4.38]

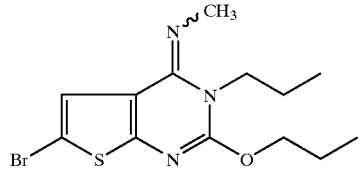

In a sulfonation flask, 1.2 g (0.0045 mol) (3-propyl-2-propoxy-3H-thieno[2,3-d]-pyrimidine-4-ylidene)

methylamine are dissolved in 15 ml of absolute pyridine. Then the internal temperature is raised to 60° C. and 1.2 g (0.0068 mol) N-bromosuccinimide are added in three portions. After stirring for 3 hours at 60° C., the pyridine is distilled off in a water jet vacuum and the residue taken up in ethylacetate. The organic phase is washed three times with water and after drying the organic phase over $Na_2SO_4$ the solvent is removed in a water jet vacuum. The raw material is purified by column chromatography over silica gel (eluant: hexane/ethylacetate 3:1). Yield: 1.2 g of (6-bromo-3-propyl-2-propoxy-3H-thieno[2,3-d]pyrimidine-4-ylidene)methylamine in the form of a brownish oil ($^1$H-NMR-data see table 5).

Example P-12

(6-Bromo-2-butoxy-3-propyl-3H-quinazolin-4-ylidene)methylamine

[cmpd. no 1.86]

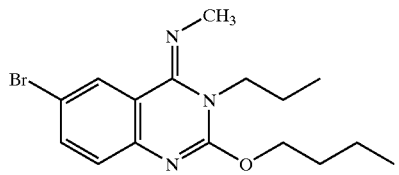

In a sulfonation flask, 1.5 g (0.0055 mol) (2-butoxy-3-propyl-3H-quinozalin-4-ylidene)methylamine are dissolved in 15 ml of absolute pyridine. Then the internal temperature is raised to 60° C. and 1.22 g (0.0068 mol) N-bromosuccinimide are added in four portions. After stirring for 4 hours at 70° C., the pyridine is distilled off in a water jet vacuum and the residue taken up in ethylacetate. The organic phase is washed three times with water and after drying the organic phase over $Na_2SO_4$ the solvent is removed in a water jet vacuum. The crude product is purified by column chromatography over silica gel (eluant: hexane/ethylacetate 4:1). Yield: 0.7 g of (6-bromo-2-butoxy-3-propyl-3H-quinozalin-4-ylidene)methylamine in the form of an orange oil ($^1$H-NMR-data see table 5).

Example P-13

(6-chloro-2-propoxy-3-propyl-3H-thieno[2,3-d]pyrimidin-4-ylidene)carbamic Acid Methylester

[cmpd. no. 4.120]

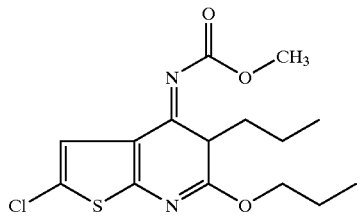

In a sulfonation flask, 1.0 g (0.0035 mol) 6-chloro-2-propoxy-3-propyl-3H-thieno[2,3-d]pyrimidine-4-ylideneamine and 0.31 g (0.0038 mol) of absolute pyridine are dissolved in 15 ml of absolute THF. Then a mixture of 0.36 g (0.0038 mol)methylchloroformiate and 5 ml absolute THF are added dropwise at room temperature. Then the resulting mixture is stirred for 1 hour at room temperature and 1 hour at 50° C. Solids are filtered off and then the solution is concentrated in a water jet vacuum. The raw material is purified by column chromatography over silica gel (eluant: hexane/ethylacetate 5:1). Yield: 0.35 g of (6-chloro-2-propoxy-3-propyl-3H-thieno[2,3-d]pyrimidine-4-ylidene)carbamic acid methylester having a melting point of 65–67° C.

TABLE 1

A = Phenyl

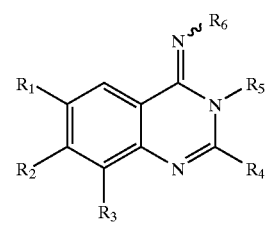

pure E- or Z-isomers of mixtures thereof

| Cmpd. no. | $R_1$ | $R_2$ | $R_3$ | $R_4$ | $R_5$ | $R_6$ | phys. data m.p. ° C. |
|---|---|---|---|---|---|---|---|
| 1.1 | Cl | H | H | Et | Et | H | |
| 1.2 | Cl | H | H | n-Propyl | Et | H | |
| 1.3 | Cl | H | H | n-Propyl | n-Propyl | H | |
| 1.4 | Cl | H | H | n-Propyl | n-Propyl | H | |
| 1.5 | Cl | H | H | n-Butyl | n-Propyl | H | |
| 1.6 | Cl | H | H | n-Butyl | n-Butyl | H | |
| 1.7 | Cl | H | H | O—Et | n-Propyl | H | |
| 1.8 | Cl | H | H | O-n-Propyl | n-Propyl | H | |
| 1.9 | Cl | H | H | O-n-Propyl | n-Butyl | H | |
| 1.10 | Cl | H | H | O-n-Propyl | i-Butyl | H | |
| 1.11 | Cl | H | H | O-n-Butyl | n-Propyl | H | |
| 1.12 | Cl | H | H | O-n-Butyl | n-Butyl | H | |
| 1.13 | Br | H | H | Et | Et | H | |
| 1.14 | Br | H | H | n-Propyl | Et | H | |
| 1.15 | Br | H | H | n-Propyl | n-Propyl | H | |

TABLE 1-continued

A = Phenyl

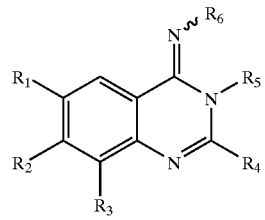

pure E- or Z-isomers of mixtures thereof

| Cmpd. no. | R$_1$ | R$_2$ | R$_3$ | R$_4$ | R$_5$ | R$_6$ | phys. data m.p. ° C. |
|---|---|---|---|---|---|---|---|
| 1.16 | Br | H | H | n-Propyl | n-Butyl | H | |
| 1.17 | Br | H | H | n-Butyl | n-Propyl | H | |
| 1.18 | Br | H | H | n-Butyl | n-Butyl | H | |
| 1.19 | Br | H | H | O—Et | n-Propyl | H | |
| 1.20 | Br | H | H | O-n-Propyl | n-Propyl | H | oil |
| 1.21 | Br | H | H | O-n-Propyl | n-Butyl | H | |
| 1.22 | Br | H | H | O-n-Propyl | i-Butyl | H | |
| 1.23 | Br | H | H | O-n-Butyl | n-Propyl | H | |
| 1.24 | Br | H | H | O-n-Butyl | n-Butyl | H | |
| 1.25 | I | H | H | Et | Et | H | |
| 1.26 | I | H | H | n-Propyl | Et | H | |
| 1.27 | I | H | H | n-Propyl | n-Propyl | H | |
| 1.28 | I | H | H | n-Propyl | n-Butyl | H | |
| 1.29 | I | H | H | n-Butyl | n-Propyl | H | |
| 1.30 | I | H | H | n-Butyl | n-Butyl | H | |
| 1.31 | I | H | H | O—Et | n-Propyl | H | |
| 1.32 | I | H | H | O-n-Propyl | n-Propyl | H | |
| 1.33 | I | H | H | O-n-Propyl | n-Butyl | H | |
| 1.34 | I | H | H | O-n-Propyl | i-Butyl | H | |
| 1.35 | I | H | H | O-n-Butyl | n-Propyl | H | |
| 1.36 | I | H | H | O-n-Butyl | n-Butyl | H | |
| 1.37 | H | Cl | H | n-Propyl | n-Propyl | H | |
| 1.38 | H | Cl | H | n-Propyl | n-Butyl | H | |
| 1.39 | H | Cl | H | n-Butyl | n-Propyl | H | |
| 1.40 | H | Cl | H | n-Butyl | n-Butyl | H | |
| 1.41 | H | Cl | H | O-n-Propyl | n-Propyl | H | |
| 1.42 | H | Cl | H | O-n-Propyl | n-Butyl | H | |
| 1.43 | H | Cl | H | O-n-Propyl | i-Butyl | H | |
| 1.44 | H | Cl | H | O-n-Butyl | n-Propyl | H | |
| 1.45 | H | Cl | H | O-n-Butyl | O-n-Butyl | H | |
| 1.46 | Cl | H | Cl | n-Propyl | n-Propyl | H | |
| 1.47 | Cl | H | Cl | n-Butyl | n-Butyl | H | |
| 1.48 | Cl | H | Cl | O-n-Propyl | n-Propyl | H | |
| 1.49 | Cl | H | Cl | O-n-Propyl | n-Butyl | H | |
| 1.50 | Br | H | Br | n-Propyl | n-Propyl | H | |
| 1.51 | Br | H | Br | n-Propyl | n-Butyl | H | |
| 1.52 | Br | H | Br | n-Propyl | i-Butyl | H | |
| 1.53 | Br | H | Br | n-Butyl | n-Propyl | H | |
| 1.54 | Br | H | Br | n-Butyl | n-Butyl | H | |
| 1.55 | Br | H | Br | O-n-Propyl | n-Propyl | H | |
| 1.56 | Br | H | Br | O-n-Propyl | n-Butyl | H | |
| 1.57 | Br | H | Br | O-n-Propyl | i-Butyl | H | |
| 1.58 | Br | H | Br | O-n-Butyl | n-Propyl | H | |
| 1.59 | Br | H | Br | O-n-Butyl | n-Butyl | H | |
| 1.60 | I | H | I | n-Propyl | n-Propyl | H | |
| 1.61 | I | H | I | n-Propyl | n-Butyl | H | |
| 1.62 | I | H | I | n-Propyl | i-Butyl | H | |
| 1.63 | I | H | I | n-Butyl | n-Propyl | H | |
| 1.64 | I | H | I | n-Butyl | n-Butyl | H | |
| 1.65 | I | H | I | O-n-Propyl | n-Propyl | H | |
| 1.66 | I | H | I | O-n-Propyl | n-Butyl | H | |
| 1.67 | I | H | I | O-n-Propyl | i-Butyl | H | |
| 1.68 | I | H | I | O-n-Butyl | n-Propyl | H | |
| 1.69 | I | H | I | O-n-Butyl | n-Butyl | H | |
| 1.70 | Cl | H | H | n-Propyl | n-Propyl | Me | |
| 1.71 | Cl | H | H | n-Propyl | n-Butyl | Me | |

TABLE 1-continued

A = Phenyl

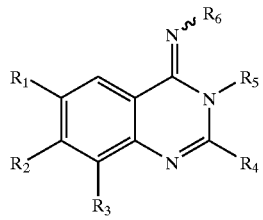

pure E- or Z-isomers of mixtures thereof

| Cmpd. no. | $R_1$ | $R_2$ | $R_3$ | $R_4$ | $R_5$ | $R_6$ | phys. data m.p. ° C. |
|---|---|---|---|---|---|---|---|
| 1.72 | Cl | H | H | n-Butyl | n-Propyl | Me | 58–60 |
| 1.73 | Cl | H | H | n-Butyl | n-Butyl | Me | |
| 1.74 | Cl | H | H | O-n-Propyl | n-Propyl | Me | 53–55 |
| 1.75 | Cl | H | H | O-n-Propyl | n-Butyl | Me | |
| 1.76 | Cl | H | H | O-n-Propyl | i-Butyl | Me | |
| 1.77 | Cl | H | H | O-n-Butyl | n-Propyl | Me | oil; $^1$H-NMR |
| 1.78 | Cl | H | H | O-n-Butyl | n-Butyl | Me | |
| 1.79 | Br | H | H | n-Propyl | n-Propyl | Me | |
| 1.80 | Br | H | H | n-Propyl | n-Butyl | Me | |
| 1.81 | Br | H | H | n-Butyl | n-Propyl | Me | 61–64 |
| 1.82 | Br | H | H | n-Butyl | n-Butyl | Me | |
| 1.83 | Br | H | H | O-n-Propyl | n-Propyl | Me | oil; $^1$H-NMR |
| 1.84 | Br | H | H | O-n-Propyl | n-Butyl | Me | |
| 1.85 | Br | H | H | O-n-Propyl | i-Butyl | Me | |
| 1.86 | Br | H | H | O-n-Butyl | n-Propyl | Me | oil; $^1$H-NMR |
| 1.87 | Br | H | H | O-n-Butyl | n-Butyl | Me | |
| 1.88 | I | H | H | n-Propyl | n-Propyl | Me | |
| 1.89 | I | H | H | n-Propyl | n-Butyl | Me | |
| 1.90 | I | H | H | n-Butyl | n-Propyl | Me | |
| 1.91 | I | H | H | n-Butyl | n-Butyl | Me | |
| 1.92 | I | H | H | O-n-Propyl | n-Propyl | Me | |
| 1.93 | I | H | H | O-n-Propyl | n-Butyl | Me | |
| 1.94 | I | H | H | O-n-Propyl | i-Butyl | Me | |
| 1.95 | I | H | H | O-n-Butyl | n-Propyl | Me | |
| 1.96 | I | H | H | O-n-Butyl | n-Butyl | Me | |
| 1.97 | H | Cl | H | n-Propyl | n-Butyl | Me | |
| 1.98 | H | Cl | H | n-Butyl | n-Propyl | Me | |
| 1.99 | H | Cl | H | n-Butyl | n-Butyl | Me | |
| 1.100 | H | Cl | H | O-n-Propyl | n-Propyl | Me | |
| 1.101 | H | Cl | H | O-n-Propyl | n-Butyl | Me | |
| 1.102 | Cl | H | Cl | n-Propyl | n-Propyl | Me | |
| 1.103 | Cl | H | Cl | n-Propyl | n-Butyl | Me | |
| 1.104 | Cl | H | Cl | n-Butyl | n-Propyl | Me | |
| 1.105 | Cl | H | Cl | n-Butyl | n-Butyl | Me | |
| 1.106 | Cl | H | Cl | O-n-Propyl | n-Propyl | Me | |
| 1.107 | Cl | H | Cl | O-n-Propyl | n-Butyl | Me | |
| 1.108 | Cl | H | Cl | O-n-Propyl | i-Butyl | Me | |
| 1.109 | Cl | H | Cl | O-n-Butyl | n-Propyl | Me | |
| 1.110 | Cl | H | Cl | O-n-Butyl | n-Butyl | Me | |
| 1.111 | Br | H | Br | n-Propyl | n-Propyl | Me | |
| 1.112 | Br | H | Br | n-Propyl | n-Butyl | Me | |
| 1.113 | Br | H | Br | n-Butyl | n-Propyl | Me | |
| 1.114 | Br | H | Br | n-Butyl | n-Butyl | Me | |
| 1.115 | Br | H | Br | O-n-Propyl | n-Propyl | Me | |
| 1.116 | Br | H | Br | O-n-Propyl | n-Butyl | Me | |
| 1.117 | Br | H | Br | O-n-Propyl | i-Butyl | Me | |
| 1.18 | Br | H | Br | O-n-Butyl | n-Propyl | Me | |
| 1.119 | Br | H | Br | O-n-Butyl | n-Butyl | Me | |
| 1.120 | I | H | I | n-Propyl | n-Propyl | Me | |
| 1.121 | I | H | I | n-Propyl | n-Butyl | Me | |
| 1.122 | I | H | I | n-Butyl | n-Propyl | Me | |
| 1.123 | I | H | I | n-Butyl | n-Butyl | Me | |

TABLE 1-continued

A = Phenyl

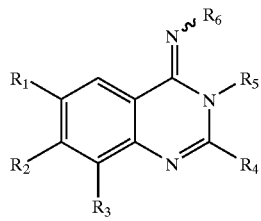

pure E- or Z-isomers of mixtures thereof

| Cmpd. no. | $R_1$ | $R_2$ | $R_3$ | $R_4$ | $R_5$ | $R_6$ | phys. data m.p. ° C. |
|---|---|---|---|---|---|---|---|
| 1.124 | I | H | I | O-n-Propyl | n-Propyl | Me | |
| 1.125 | I | H | I | O-n-Propyl | n-Butyl | Me | |
| 1.126 | I | H | I | O-n-Propyl | i-Butyl | Me | oil |
| 1.127 | I | H | I | O-n-Butyl | n-Propyl | Me | |
| 1.128 | I | H | I | O-n-Butyl | n-Butyl | Me | |
| 1.129 | Cl | H | H | n-Propyl | n-Propyl | Et | |
| 1.130 | Cl | H | H | n-Propyl | n-Butyl | Et | |
| 1.131 | Cl | H | H | n-Butyl | n-Propyl | Et | |
| 1.132 | Cl | H | H | n-Butyl | n-Butyl | Et | |
| 1.133 | Cl | H | H | O-n-Propyl | n-Propyl | Et | |
| 1.134 | Cl | H | H | O-n-Propyl | n-Butyl | Et | |
| 1.135 | Cl | H | H | O-n-Propyl | i-Butyl | Et | |
| 1.136 | Cl | H | H | O-n-Butyl | n-Propyl | Et | |
| 1.137 | Cl | H | H | O-n-Butyl | n-Butyl | Et | |
| 1.138 | Br | H | H | n-Propyl | n-Butyl | Et | |
| 1.139 | Br | H | H | n-Butyl | n-Propyl | Et | |
| 1.140 | Br | H | H | n-Butyl | n-Butyl | Et | |
| 1.141 | Br | H | H | O-n-Propyl | n-Propyl | Et | |
| 1.142 | Br | H | H | O-n-Propyl | n-Butyl | Et | |
| 1.143 | Br | H | H | O-n-Propyl | i-Butyl | Et | |
| 1.144 | Br | H | H | O-n-Butyl | n-Propyl | Et | |
| 1.145 | Br | H | H | O-n-Butyl | n-Butyl | Et | |
| 1.146 | I | H | H | n-Butyl | n-Butyl | Et | |
| 1.147 | I | H | H | O-n-Propyl | n-Propyl | Et | |
| 1.148 | Br | H | Br | O-n-Propyl | n-Propyl | Et | |
| 1.149 | Cl | H | H | n-Propyl | n-Propyl | n-Propyl | |
| 1.150 | Cl | H | H | n-Butyl | n-Propyl | n-Propyl | |
| 1.151 | Cl | H | H | n-Butyl | n-Butyl | n-Propyl | |
| 1.152 | Cl | H | H | O-n-Propyl | n-Propyl | n-Propyl | 50–51 |
| 1.153 | Cl | H | H | O-n-Propyl | n-Butyl | n-Propyl | |
| 1.154 | Br | H | H | n-Butyl | n-Propyl | n-Propyl | |
| 1.155 | Br | H | H | O-n-Propyl | n-Propyl | n-Propyl | |
| 1.156 | Cl | H | H | n-Propyl | n-Propyl | n-Butyl | |
| 1.157 | Cl | H | H | N-Propyl | n-Butyl | n-Butyl | |
| 1.158 | Cl | H | H | n-Butyl | n-Butyl | n-Butyl | |
| 1.159 | Cl | H | H | O-n-Propyl | n-Propyl | n-Butyl | |
| 1.160 | Cl | H | H | O-n-Propyl | n-Butyl | n-Butyl | 38–40 |
| 1.161 | Cl | H | H | n-Propyl | n-Propyl | Allyl | |
| 1.162 | Cl | H | H | n-Propyl | n-Butyl | Allyl | |
| 1.163 | Cl | H | H | n-Butyl | n-Propyl | Allyl | |
| 1.164 | Cl | H | H | n-Butyl | n-Butyl | Allyl | |
| 1.165 | Cl | H | H | O-n-Propyl | n-Propyl | Allyl | |
| 1.166 | Cl | H | H | O-n-Propyl | n-Butyl | Allyl | |
| 1.167 | Cl | H | H | O-n-Butyl | n-Propyl | Allyl | |
| 1.168 | Br | H | H | n-Propyl | n-Butyl | Allyl | |
| 1.169 | Br | H | H | n-Butyl | n-Propyl | Allyl | |
| 1.170 | Br | H | H | n-Butyl | n-Butyl | Allyl | |
| 1.171 | Br | H | H | O-n-Propyl | n-Propyl | Allyl | |
| 1.172 | Br | N | N | O-n-Propyl | n-Butyl | Allyl | |
| 1.173 | I | H | H | O-n-Propyl | n-Propyl | Allyl | |
| 1.174 | Cl | H | H | n-Propyl | n-Butyl | $CH_2C{\equiv}CH$ | |
| 1.175 | Cl | H | H | n-Butyl | n-Propyl | $CH_2C{\equiv}CH$ | |
| 1.176 | Cl | H | H | n-Butyl | n-Butyl | $CH_2C{\equiv}CH$ | |
| 1.177 | Cl | H | H | O-n-Propyl | n-Propyl | $CH_2C{\equiv}CH$ | |

TABLE 1-continued

A = Phenyl pure E- or Z-isomers of mixtures thereof

| Cmpd. no. | $R_1$ | $R_2$ | $R_3$ | $R_4$ | $R_5$ | $R_6$ | phys. data m.p. °C. |
|---|---|---|---|---|---|---|---|
| 1.178 | Cl | H | H | O-n-Propyl | n-Butyl | CH$_2$C≡CH | |
| 1.179 | Br | H | H | n-Propyl | n-Butyl | CH$_2$C≡CH | |
| 1.180 | Br | H | H | n-Butyl | n-Propyl | CH$_2$C≡CH | |
| 1.181 | Br | H | H | n-Butyl | n-Butyl | CH$_2$C≡CH | |
| 1.182 | Br | H | H | O-n-Propyl | n-Propyl | CH$_2$C≡CH | |
| 1.183 | Br | H | H | O-n-Propyl | n-Butyl | CH$_2$C≡CH | |
| 1.184 | Br | H | H | O-n-Butyl | n-Propyl | CH$_2$C≡CH | |
| 1.185 | Cl | H | H | n-Propyl | n-Butyl | CN | |
| 1.186 | Cl | H | H | n-Butyl | n-Propyl | CN | |
| 1.187 | Cl | H | H | n-Butyl | n-Butyl | CN | |
| 1.188 | Cl | H | H | O-n-Propyl | n-Propyl | CN | |
| 1.189 | Cl | H | H | O-n-Propyl | n-Butyl | CN | |
| 1.190 | Br | H | H | n-Propyl | n-Butyl | CN | |
| 1.191 | Br | H | H | n-Butyl | n-Propyl | CN | |
| 1.192 | Br | H | H | n-Butyl | n-Butyl | CN | |
| 1.193 | Br | H | H | O-n-Propyl | n-Propyl | CN | oil |
| 1.194 | Br | H | H | O-n-Propyl | n-Butyl | CN | |
| 1.195 | Br | H | H | O-n-Butyl | n-Propyl | CN | |
| 1.196 | I | H | H | n-Butyl | n-Butyl | CN | |
| 1.197 | I | H | H | O-n-Propyl | n-Propyl | CN | |
| 1.198 | I | H | H | O-n-Propyl | n-Butyl | CN | |
| 1.199 | Cl | H | H | n-Propyl | n-Butyl | Cl | |
| 1.200 | Cl | H | H | n-Butyl | n-Propyl | Cl | |
| 1.201 | Cl | H | H | n-Butyl | n-Butyl | Cl | |
| 1.202 | Cl | H | H | O-n-Propyl | n-Propyl | Cl | |
| 1.203 | Cl | H | H | O-n-Propyl | n-Butyl | Cl | |
| 1.204 | Br | H | H | n-Butyl | n-Butyl | Cl | |
| 1.205 | Br | H | H | O-n-Propyl | n-Propyl | Cl | |
| 1.206 | Br | H | H | O-n-Propyl | n-Butyl | Cl | |
| 1.207 | I | H | H | n-Butyl | n-Butyl | Cl | |
| 1.208 | I | H | H | O-n-Propyl | n-Propyl | Cl | |
| 1.209 | I | H | H | O-n-Propyl | n-Butyl | Cl | |
| 1.210 | Cl | H | H | n-Butyl | n-Butyl | NO$_2$ | |
| 1.211 | Cl | H | H | O-n-Propyl | n-Propyl | NO$_2$ | |
| 1.212 | Cl | H | H | O-n-Propyl | n-Butyl | NO$_2$ | |
| 1.213 | Br | H | H | n-Butyl | n-Butyl | NO$_2$ | |
| 1.214 | Br | H | H | O-n-Propyl | n-Propyl | NO$_2$ | |
| 1.215 | Br | H | H | O-n-Propyl | n-Butyl | NO$_2$ | |
| 1.216 | I | H | H | n-Butyl | n-Butyl | NO$_2$ | |
| 1.217 | I | H | H | O-n-Propyl | n-Propyl | NO$_2$ | |
| 1.218 | I | H | H | O-n-Propyl | n-Butyl | NO$_2$ | |
| 1.219 | Cl | H | H | n-Butyl | n-Butyl | COOMe | oil |
| 1.220 | Cl | H | H | O-n-Propyl | n-Propyl | COOMe | |
| 1.221 | Br | H | H | O-n-Propyl | n-Propyl | COMe | |
| 1.222 | Br | H | H | O-n-Propyl | n-Propyl | COEt | |
| 1.223 | Br | H | H | O-n-Propyl | n-Propyl | COPhenyl | |
| 1.224 | Br | H | H | O-n-Propyl | n-Propyl | CO-p-F-phenyl | |

TABLE 1-continued

A = Phenyl

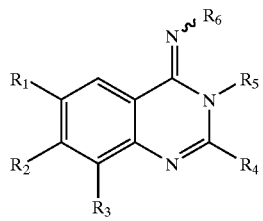

pure E- or Z-isomers of mixtures thereof

| Cmpd. no. | R₁ | R₂ | R₃ | R₄ | R₅ | R₆ | phys. data m.p. ° C. |
|---|---|---|---|---|---|---|---|
| 1.225 | Br | H | H | O-n-Propyl | n-Propyl | CO-2-pyridyl | |
| 1.226 | Br | H | H | O-n-Propyl | n-Propyl | CO-3-pyridyl | |
| 1.227 | Br | H | H | O-n-Propyl | n-Propyl | CO-3-(2-Cl-pyridyl) | |
| 1.228 | Br | H | H | O-n-Propyl | n-Propyl | CO-2-Thienyl | |
| 1.229 | Br | H | H | O-n-Propyl | n-Propyl | COCH$_2$OMe | |
| 1.230 | Br | H | H | O-n-Propyl | n-Propyl | CH$_2$COOMe | |

TABLE 2

Compounds of the general formula (I); $R_2 = R_3 = H$
A = Pyridyl

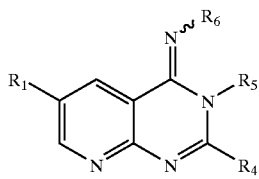

(I)

pure E- or Z-isomers or mixtures thereof

| Cmpd. no. | R₁ | R₄ | R₅ | R₆ | phys. data ° C. |
|---|---|---|---|---|---|
| 2.1. | Cl | n-Propyl | n-Propyl | H | |
| 2.2. | Cl | n-Propyl | n-Butyl | H | |
| 2.3. | Cl | n-Butyl | n-Propyl | H | |
| 2.4. | Cl | n-Butyl | n-Butyl | H | |
| 2.5. | Cl | O-n-Propyl | n-Propyl | H | |
| 2.6. | Cl | O-n-Propyl | n-Butyl | H | |
| 2.7. | Br | n-Propyl | n-Propyl | H | |
| 2.8. | Br | n-Propyl | n-Butyl | H | |
| 2.9. | Br | n-Butyl | n-Propyl | H | |
| 2.10. | Br | n-Butyl | n-Butyl | H | |
| 2.11. | Br | O-n-Propyl | n-Propyl | H | oil |
| 2.12. | Br | O-n-Propyl | n-Butyl | H | |
| 2.13. | Cl | n-Propyl | n-Propyl | Me | |
| 2.14. | Cl | n-Propyl | n-Butyl | Me | |
| 2.15. | Cl | n-Butyl | n-Propyl | Me | |
| 2.16. | Cl | n-Butyl | n-Butyl | Me | |
| 2.17. | Cl | O-n-Propyl | n-Propyl | Me | |
| 2.18. | Cl | O-n-Propyl | n-Butyl | Me | |
| 2.19. | Br | n-Propyl | n-Propyl | Me | |
| 2.20. | Br | n-Propyl | n-Butyl | Me | |
| 2.21. | Br | n-Butyl | n-Propyl | Me | |
| 2.22. | Br | n-Butyl | n-Butyl | Me | |
| 2.23. | Br | O-n-Propyl | n-Propyl | Me | |
| 2.24. | Br | O-n-Propyl | n-Butyl | Me | |
| 2.25. | Cl | n-Butyl | n-Butyl | Et | |
| 2.26. | Cl | O-n-Propyl | n-Propyl | Et | |
| 2.27. | I | n-Butyl | n-Butyl | Et | |
| 2.28. | I | O-n-Propyl | n-Butyl | Et | |
| 2.29. | Cl | n-Butyl | n-Butyl | n-Propyl | |
| 2.30. | Cl | O-n-Propyl | n-Propyl | n-Propyl | |
| 2.31. | Br | n-Butyl | n-Butyl | n-Propyl | |

TABLE 2-continued

Compounds of the general formula (I); $R_2 = R_3 = H$
A = Pyridyl

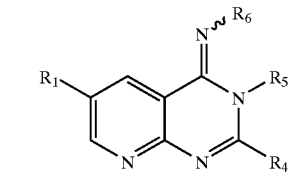

(I)

pure E- or Z-isomers or mixtures thereof

| Cmpd. no. | R₁ | R₄ | R₅ | R₆ | phys. data ° C. |
|---|---|---|---|---|---|
| 2.32. | Br | O-n-Propyl | n-Propyl | n-Propyl | |
| 2.33. | Cl | n-Butyl | n-Butyl | Allyl | |
| 2.34. | Cl | O-n-Propyl | n-Propyl | Allyl | |
| 2.35. | Br | n-Butyl | n-Butyl | Allyl | |
| 2.36. | Br | O-n-Propyl | n-Butyl | Allyl | |
| 2.37. | Cl | n-Butyl | n-Butyl | CH$_2$C≡CH | |
| 2.38. | Cl | O-n-Propyl | n-Propyl | CH$_2$C≡CH | |
| 2.39. | Br | n-Butyl | n-Butyl | CH$_2$C≡CH | |
| 2.40. | Br | O-n-Propyl | n-Propyl | CH$_2$C≡CH | |
| 2.41. | Cl | n-Butyl | n-Butyl | CN | oil |
| 2.42. | Cl | n-Butyl | n-Butyl | CN | |
| 2.43. | Cl | n-Butyl | n-Butyl | Cl | |
| 2.44. | Cl | n-Butyl | n-Propyl | Cl | |
| 2.45. | Br | n-Butyl | n-Butyl | NO$_2$ | |
| 2.46. | Br | O-n-Propyl | n-Propyl | NO$_2$ | |
| 2.47. | Br | O-n-Propyl | n-Propyl | COOMe | |
| 2.48. | Br | O-n-Propyl | n-Propyl | COMe | |

TABLE 3

Compounds of the general formula (I); $R_2$ = H
A = Thienyl[3.2-d]

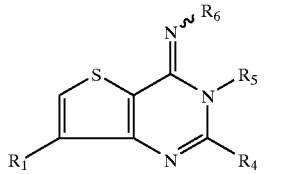

(I)

pure E- or Z-isomers or mixtures thereof

| Cmpd. no. | $R_1$ | $R_4$ | $R_5$ | $R_6$ | phys. data ° C. |
|---|---|---|---|---|---|
| 3.1. | Br | n-Butyl | n-Butyl | H | |
| 3.2. | Br | O-n-Propyl | n-Propyl | H | |
| 3.3. | Cl | n-Butyl | n-Butyl | H | |
| 3.4. | Cl | O-n-Propyl | n-Butyl | H | |
| 3.5. | Br | n-Butyl | n-Butyl | Me | |
| 3.6. | Br | O-n-Propyl | n-Propyl | Me | oil |
| 3.7. | Cl | n-Butyl | n-Butyl | Me | |
| 3.8. | Cl | O-n-Propyl | n-Propyl | Me | |
| 3.9. | Br | n-Butyl | n-Butyl | Allyl | |
| 3.10. | Br | O-n-Propyl | n-Propyl | Allyl | |
| 3.11. | Br | n-Butyl | n-Butyl | $CH_2C{\equiv}CH$ | |
| 3.12. | Br | O-n-Propyl | n-Propyl | $CH_2C{\equiv}CH$ | |
| 3.13. | Br | n-Butyl | n-Butyl | CN | |
| 3.14. | Br | O-n-Propyl | n-Propyl | CN | |
| 3.15. | Cl | n-Butyl | n-Butyl | Cl | |
| 3.16. | Cl | O-n-Propyl | n-Propyl | Cl | |

TABLE 4

Compounds of the general formula (I); $R_2$ = H
A = Thienyl[2.3-d]

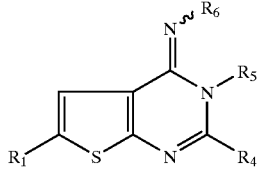

(I)

pure E- or Z-isomers or mixtures thereof

| Cmpd. no. | $R_1$ | $R_4$ | $R_5$ | $R_6$ | phys. data m.p. ° C. |
|---|---|---|---|---|---|
| 4.1. | H | n-Propyl | n-Propyl | H | |
| 4.2. | H | n-Propyl | n-Butyl | H | |
| 4.3. | H | n-Butyl | n-Propyl | H | oil ($^1$H-NMR) |
| 4.4. | H | n-Butyl | n-Butyl | H | |
| 4.5. | H | O-n-Propyl | n-Propyl | H | 61–63 |
| 4.6. | H | O-n-Propyl | n-Butyl | H | 55–57 |
| 4.7. | H | O-n-Propyl | i-Butyl | H | |
| 4.8. | H | O-n-Butyl | n-Propyl | H | |
| 4.9. | H | O-n-Butyl | n-Butyl | H | |
| 4.10. | Cl | n-Butyl | n-Propyl | H | |
| 4.11. | Cl | n-Butyl | n-Butyl | H | 84–85 |
| 4.12. | Cl | O-n-Propyl | n-Propyl | H | |
| 4.13. | Cl | O-n-Propyl | n-Butyl | H | |
| 4.14. | Cl | O-n-Propyl | i-Butyl | H | |
| 4.15. | Cl | O-n-Butyl | n-Propyl | H | |
| 4.16. | Cl | O-n-Butyl | n-Butyl | H | |
| 4.17. | Br | n-Butyl | n-Propyl | H | |
| 4.18. | Br | n-Butyl | n-Butyl | H | |
| 4.19. | Br | O-n-Propyl | n-Propyl | H | |

TABLE 4-continued

Compounds of the general formula (I); $R_2$ = H
A = Thienyl[2.3-d]

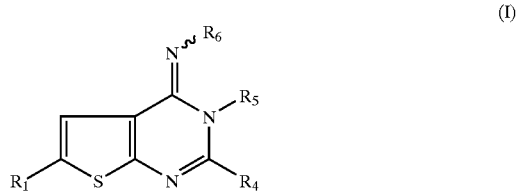

(I)

pure E- or Z-isomers or mixtures thereof

| Cmpd. no. | $R_1$ | $R_4$ | $R_5$ | $R_6$ | phys. data m.p. °C. |
|---|---|---|---|---|---|
| 4.20. | Br | O-n-Propyl | n-Propyl | H | |
| 4.21. | Br | O-n-Propyl | n-Butyl | H | |
| 4.22. | Br | O-n-Propyl | i-Butyl | H | |
| 4.23. | Br | O-n-Butyl | n-Propyl | H | |
| 4.24. | Br | O-n-Butyl | n-Butyl | H | |
| 4.25. | Cl | n-Propyl | n-Propyl | Me | |
| 4.26. | Cl | n-Propyl | n-Butyl | Me | |
| 4.27. | Cl | n-Butyl | n-Propyl | Me | oil ($^1$H-NMR) |
| 4.28. | Cl | n-Butyl | n-Butyl | Me | |
| 4.29. | Cl | O-n-Propyl | n-Propyl | Me | oil ($^1$H-NMR) |
| 4.30. | Cl | O-n-Propyl | n-Butyl | Me | oil ($^1$H-NMR) |
| 4.31. | Cl | O-n-Propyl | i-Butyl | Me | |
| 4.32. | Cl | O-n-Butyl | n-Propyl | Me | |
| 4.33. | Cl | O-n-Butyl | n-Butyl | Me | |
| 4.34. | Br | n-Propyl | n-Propyl | Me | |
| 4.35. | Br | n-Propyl | n-Butyl | Me | |
| 4.36. | Br | n-Butyl | n-Propyl | Me | oil ($^1$H-NMR) |
| 4.37. | Br | n-Butyl | n-Butyl | Me | oil ($^1$H-NMR) |
| 4.38. | Br | O-n-Propyl | n-Propyl | Me | oil ($^1$H-NMR) |
| 4.39. | Br | O-n-Propyl | n-Butyl | Me | oil ($^1$H-NMR) |
| 4.40. | Br | O-n-Propyl | i-Butyl | Me | |
| 4.41. | Br | O-n-Butyl | n-Propyl | Me | |
| 4.42. | Br | O-n-Butyl | n-Butyl | Me | |
| 4.43. | Cl | n-Butyl | n-Propyl | Et | 73–74 |
| 4.44. | Cl | n-Butyl | n-Butyl | Et | |
| 4.45. | Cl | O-n-Propyl | n-Propyl | Et | oil ($^1$H-NMR) |
| 4.46. | Cl | O-n-Propyl | n-Butyl | Et | |
| 4.47. | Cl | O-n-Butyl | n-Butyl | Et | |
| 4.48. | Br | n-Butyl | n-Propyl | Et | |
| 4.49. | Br | n-Butyl | n-Butyl | Et | |
| 4.50. | Br | O-n-Propyl | n-Propyl | Et | |
| 4.51. | Br | O-n-Propyl | n-Butyl | Et | |
| 4.52. | Cl | n-Butyl | n-Butyl | n-Propyl | |
| 4.53. | Cl | n-O-Propyl | n-Propyl | n-Propyl | |
| 4.54. | Cl | n-O-Propyl | n-Butyl | n-Propyl | |
| 4.55. | Br | n-Butyl | n-Butyl | n-Propyl | |
| 4.56. | Br | O-n-Propyl | n-Propyl | n-Propyl | |
| 4.57. | Br | O-n-Propyl | n-Butyl | n-Propyl | |
| 4.58. | Cl | n-Propyl | n-Propyl | Allyl | |
| 4.59. | Cl | n-Propyl | n-Butyl | Allyl | |
| 4.60. | Cl | n-Butyl | n-Propyl | Allyl | |
| 4.61. | Cl | n-Butyl | n-Butyl | Allyl | |
| 4.62. | Cl | O-n-Propyl | n-Propyl | Allyl | oil ($^1$H-NMR) |
| 4.63. | Cl | O-n-Propyl | n-Butyl | Allyl | |
| 4.64. | Cl | O-n-Propyl | i-Butyl | Allyl | |
| 4.65. | Cl | O-n-Butyl | n-Propyl | Allyl | |
| 4.66. | Cl | O-n-Butyl | n-Butyl | Allyl | |
| 4.67. | Br | n-Propyl | n-Propyl | Allyl | |
| 4.68. | Br | n-Propyl | n-Butyl | Allyl | |
| 4.69. | Br | n-Butyl | n-Propyl | Allyl | |
| 4.70. | Br | n-Butyl | n-Butyl | Allyl | |
| 4.71. | Br | O-n-Propyl | n-Propyl | Allyl | |
| 4.72. | Br | O-n-Propyl | n-Butyl | Allyl | |

TABLE 4-continued

Compounds of the general formula (I); $R_2$ = H
A = Thienyl[2.3-d]

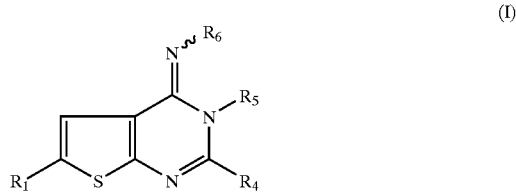

pure E- or Z-isomers or mixtures thereof

| Cmpd. no. | $R_1$ | $R_4$ | $R_5$ | $R_6$ | phys. data m.p. °C. |
|---|---|---|---|---|---|
| 4.73. | Br | O-n-Propyl | i-Butyl | Allyl | |
| 4.74. | Br | O-n-Butyl | n-Propyl | Allyl | |
| 4.75. | Br | O-n-Butyl | n-Propyl | Allyl | |
| 4.76. | Cl | n-Propyl | n-Propyl | $CH_2C{\equiv}CH$ | |
| 4.77. | Cl | n-Propyl | n-Butyl | $CH_2C{\equiv}CH$ | |
| 4.78. | Cl | n-Butyl | n-Propyl | $CH_2C{\equiv}CH$ | |
| 4.79. | Cl | n-Butyl | n-Butyl | $CH_2C{\equiv}CH$ | |
| 4.80. | Cl | O-n-Propyl | n-Propyl | $CH_2C{\equiv}CH$ | 84–86 |
| 4.81. | Cl | O-n-Propyl | n-Butyl | $CH_2C{\equiv}CH$ | |
| 4.82. | Cl | O-n-Propyl | i-Butyl | $CH_2C{\equiv}CH$ | |
| 4.83. | Cl | O-n-Butyl | n-Propyl | $CH_2C{\equiv}CH$ | |
| 4.84. | Cl | O-n-Butyl | n-Butyl | $CH_2C{\equiv}CH$ | |
| 4.85. | Br | n-Propyl | n-Propyl | $CH_2C{\equiv}CH$ | |
| 4.86. | Br | n-Propyl | n-Butyl | $CH_2C{\equiv}CH$ | |
| 4.87. | Br | n-Butyl | n-Propyl | $CH_2C{\equiv}CH$ | |
| 4.88. | Br | n-Butyl | n-Butyl | $CH_2C{\equiv}CH$ | |
| 4.89. | Br | O-n-Propyl | n-Propyl | $CH_2C{\equiv}CH$ | |
| 4.90. | Br | O-n-Propyl | n-Butyl | $CH_2C{\equiv}CH$ | |
| 4.91. | Br | O-n-Propyl | i-Butyl | $CH_2C{\equiv}CH$ | |
| 4.92. | Br | O-n-Butyl | n-Butyl | $CH_2C{\equiv}CH$ | |
| 4.93. | Br | O-n-Butyl | n-Butyl | $CH_2C{\equiv}CH$ | |
| 4.94. | Cl | n-Propyl | n-Butyl | CN | 120–122 |
| 4.95. | Cl | n-Butyl | n-Propyl | CN | |
| 4.96. | Cl | n-Butyl | n-Butyl | CN | |
| 4.97. | Cl | O-n-Propyl | n-Propyl | CN | 90–92 |
| 4.98. | Cl | O-n-Propyl | n-Butyl | CN | |
| 4.99. | Cl | O-n-Propyl | i-Butyl | CN | |
| 4.100. | Cl | O-n-Butyl | n-Propyl | CN | |
| 4.101. | Cl | O-n-Butyl | n-Butyl | CN | |
| 4.102. | Br | n-Propyl | n-Butyl | CN | |
| 4.103. | Br | n-Butyl | n-Propyl | CN | |
| 4.104. | Br | n-Butyl | n-Butyl | CN | |
| 4.105. | Br | O-n-Propyl | n-Propyl | CN | oil |
| 4.106. | Br | O-n-Propyl | n-Butyl | CN | |
| 4.107. | Br | O-n-Butyl | n-Propyl | CN | |
| 4.108. | Cl | n-Propyl | n-Butyl | Cl | |
| 4.109. | Cl | n-Butyl | n-Propyl | Cl | |
| 4.110. | Cl | n-Butyl | n-Butyl | Cl | |
| 4.111. | Cl | O-n-Propyl | n-Propyl | Cl | oil ($^1$H-NMR) |
| 4.112. | Cl | O-n-Propyl | n-Butyl | Cl | |
| 4.113. | Br | n-Butyl | n-Butyl | Cl | |
| 4.114. | Br | O-n-Propyl | n-Propyl | Cl | |
| 4.115. | Cl | n-Butyl | n-Butyl | $NO_2$ | |
| 4.116. | Cl | O-n-Propyl | n-Propyl | $NO_2$ | |
| 4.117. | Br | n-Butyl | n-Butyl | $NO_2$ | |
| 4.118. | Br | O-n-Propyl | n-Propyl | $NO_2$ | |
| 4.119. | Cl | n-Butyl | n-Butyl | COOMe | 103–104 |
| 4.120. | Cl | O-n-Propyl | n-Propyl | COOMe | 65–67 |
| 4.121. | Cl | O-n-Propyl | n-Propyl | COOEt | |
| 4.122. | Cl | n-Butyl | n-Propyl | COOEt | 84–86 |
| 4.123. | Br | n-Butyl | n-Butyl | COOEt | 98–99 |
| 4.124. | Cl | O-n-Propyl | n-Propyl | COOEt | 75–77 |
| 4.125. | Br | O-n-Propyl | n-Propyl | COOEt | |
| 4.126. | Cl | O-n-Propyl | n-Propyl | $CH_2COOEt$ | wax ($^1$H-NMR) |
| 4.127. | Br | O-n-Propyl | n-Propyl | $CH_2COOEt$ | |
| 4.128. | Cl | O-n-Propyl | n-Propyl | $COCH_2OMe$ | 57–58 |
| 4.129. | Br | O-n-Propyl | n-Propyl | $COCH_2OMe$ | |
| 4.130. | Cl | n-Butyl | n-Butyl | $COCH_2OMe$ | 60–62 |
| 4.131. | Br | n-Butyl | n-Butyl | $COCH_2OMe$ | 82–83 |
| 4.132. | Cl | O-n-Propyl | n-Propyl | $SO_2Me$ | 90–95 |

TABLE 4-continued

Compounds of the general formula (I); $R_2$ = H
A = Thienyl[2,3-d]

(I)

pure E- or Z-isomers or mixtures thereof

| Cmpd. no. | $R_1$ | $R_4$ | $R_5$ | $R_6$ | phys. data m.p. ° C. |
|---|---|---|---|---|---|
| 4.133. | Br | O-n-Propyl | n-Propyl | SO$_2$Me | |
| 4.134. | Cl | n-Butyl | n-Propyl | SO$_2$Me | 113–115 |
| 4.135. | Br | n-Butyl | n-Butyl | SO$_2$Me | |
| 4.136. | Cl | n-Butyl | n-Propyl | SO$_2$-4-Me-phenyl | |
| 4.137. | Cl | O-n-Propyl | n-Propyl | COMe | 101–103 |
| 4.138. | Br | O-n-Propyl | n-Propyl | COMe | |
| 4.139. | Cl | n-Butyl | n-Propyl | COMe | 98–99 |
| 4.140. | Cl | n-Butyl | n-Butyl | COMe | 93–94 |
| 4.141. | Br | n-Butyl | n-Propyl | COMe | |
| 4.142. | Cl | n-Butyl | n-Propyl | COEt | 73–74 |
| 4.143. | Cl | n-Butyl | n-Butyl | COEt | |
| 4.144. | Cl | n-Butyl | n-Propyl | CO-n-propyl | 79–80 |
| 4.145. | Br | n-Butyl | n-Butyl | CO-n-propyl | |
| 4.146. | Cl | n-Butyl | n-Propyl | CO-n-butyl | oil ($^1$H-NMR) |
| 4.147. | Cl | O-n-Propyl | n-Propyl | CO-n-butyl | |
| 4.148. | Cl | n-Butyl | n-Butyl | COPhenyl | 77–78 |
| 4.149. | Br | n-Butyl | n-Butyl | COPhenyl | 99–100 |
| 4.150. | Cl | O-n-Propyl | n-Propyl | COPhenyl | |
| 4.151. | Cl | n-Butyl | n-Propyl | CO-4-F-phenyl | 109–110 |
| 4.152. | Cl | n-Butyl | n-Propyl | CO-2-(3-Cl-thienyl) | 122–123 |
| 4.153. | Br | n-Butyl | n-Propyl | CO-2-(3-Cl-thienyl) | 119–121 |
| 4.154. | Cl | O-n-Propyl | n-Propyl | CO-2-(3-Cl-thienyl) | |
| 4.155. | Cl | n-Butyl | n-Propyl | CO-3-(2-Cl-pyridyl) | 128–129 |
| 4.156. | Cl | O-n-Propyl | n-Propyl | CO-3-(2-Cl-pyridyl) | |
| 4.157. | Cl | n-Butyl | n-Propyl | CO-4-(2,5-diCl-pyridyl) | 130–131 |
| 4.158. | Br | n-Butyl | n-Propyl | CO-4-(2,5-diCl-pyridyl) | 149–151 |
| 4.159. | Cl | n-Butyl | n-Propyl | (3,5-dimethylisoxazol-4-yl carbonyl) | 99–101 |
| 4.160. | Cl | O-n-Propyl | n-Propyl | (3,5-dimethylisoxazol-4-yl carbonyl) | |

TABLE 5

$^1$H-NMR-data of selected compounds

| Cmpd. No. | $^1$H-NMR-data (ppm/multiplicity/number of H's); solvent: CDCl$_3$ |
|---|---|
| 1.77 | 0.91/t/3H; 1.01/t/3H; 1.52/q/2H; 1.64/m/2H; 1.80/m/2H; 3.62/s/3H; 3.95/m/2H; 4.36/t/2H; 7.24/d/1H; 7.36/dd/1H; 8.04/d/1H |
| 1.83 | 0.91/t/3H; 1.00/t/3H; 1.68/m/2H; 1.83/m/2H; 3.61/s/3H; 3.96/m/2H; 4.32/t/2H; 7.19/d/1H; 7.49/dd/1H; 8.18/dd/1H |

TABLE 5-continued

¹H-NMR-data of selected compounds

| Cmpd. No. | ¹H-NMR-data (ppm/multiplicity/number of H's); solvent: CDCl₃ |
|---|---|
| 1.86 | 0.91/t/3H; 1.01/t/3H; 1.49/m/2H; 1.62/m/2H; 1.77/m/2H; 3.61/s/3H; 3.95/m/2H; 4.37/t/3H; 7.19/d/1H; 7.49/dd/1H; 8.17/d/1H |
| 4.3 | 0.98/t/3H; 1.02/t/3H; 1.47/m/2H; 1.73–1.82/m/4H; 2.74/t/2H; 4.10/t/2H; 7.08/d/1H; 7.23/d/1H |
| 4.27 | 0.93–1.02/m/6H; 1.48–1.90/m/6H; 2.65/t/2H; 3.36/s/3H; 3.98/m/2H; 7.46/s/1H |
| 4.29 | 0.92/t/3H; 1.02/t/3H; 1.64/m/2H; 1.77/m/2H; 3.35/s/3H; 3.98/t/2H; 4.27/t/2H; 7.42/s/1H |
| 4.30 | 0.93/t/3H; 1.02/t/3H; 1.32/m/2H; 1.51/m/2H; 1.78/m/2H; 3.36/s/3H; 4.02/t/2H; 4.27/t/2H; 7.42/s/1H |
| 4.36 | 0.91–1.02/m/6H; 1.42–1.79/m/6H; 2.63/t/2H; 3.26/s/3H; 3.95/m(broad)/2H; 7.61/s/1H |
| 4.37 | 0.96/2xt/6H; 1.40/m/4H; 1.68/m/4H; 2.63/t/2H; 3.36/s/3H; 4.00/m(broad)/2H; 7.61/s/1H |
| 4.38 | 0.91/t/3H; 1.02/t/3H; 1.60/m/2H; 1.77/m/2H; 3.36/s/3H; 3.98/t/2H; 4.27/t/2H; 7.57/s/1H |
| 4.39 | 0.93/t/3H; 1.02/t/3H; 1.33/m/2H; 1.54/m/2H; 1.78/m/2H; 4.02/t/2H; 4.27/t/2H; 7.57/s/1H |
| 4.45 | 0.91/t/3H; 0.99/t/3H; 1.27/t/3H; 1.64/m/2H; 1.78/m/2H; 3.57/q/2H; 4.01/t/2H; 4.27/t/2H; 7.30/s/1H |
| 4.62 | 0.93/t/3H; 1.02/t/3H; 1.65/m/2H; 1.79/m/2H; 4.06/t/2H; 4.21–4.31/m/4H; 5.12/dd/1H; 5.33/dd/1H; 6.03–6.17/m/1H; 7.26/s/1H |
| 4.111 | 0.94/t/3H; 1.03/t/3H; 1.65–1.85/m/4H; 4.04/t/2H; 4.32/t/2H; 8.28/s/1H |
| 4.126 | 0.93/t/3H; 1.05/t/3H; 1.30/t/3H; 1.67/m/2H; 1.81/m/2H; 4.09/m/2H; 4.25/m/4H; 4.41/s/2H; 7.18/s/1H |
| 4.143 | 0.92–1.04/m/9H; 1.45/m/4H; 1.78/m/4H; 2.54/t/2H; 2.81/t/2H; 7.08/s/1H |

Preparation Examples of the Intermediates X

Example P-14

5-Chloro-N-methyl-2-nitro-N'-propylbenzamidine (Compound 6.2)

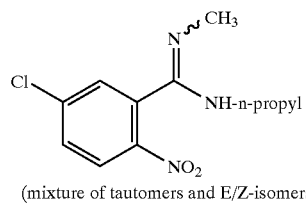

(mixture of tautomers and E/Z-isomers)

In a sulfonation flask, 3.25 g (0.015M) 5-chloro-2-nitro-3-benzoic acid methylamide were dissolved in 8.9 g (0.075M) SOCl₂ and heated at reflux temperature for 4 hours. Then the excess of SOCl₂ is removed in a water jet vacuum and the crude imidoylchloride is dissolved in 5 ml of absolute THF. The resulting solution was added dropwise to a stirred solution of 1.95 g (0.033M) 1-aminopropane in 25 ml THF. The mixture is stirred for 5 hours at reflux temperature and then the solvent is removed in a water jet vacuum. The residue is taken up in ethylacetate and the organic phase is washed twice with water and with a saturated sodiumcarbonate solution. After drying of the organic phase, the solvent is removed in a water jet vacuum, and the raw material purified by column chromatography over silica gel (eluant: hexane/ethylacetate 1:3 and then ethylacetate). Yield: 2.3 g 5-chloro-N-methyl-2-nitro-N'-propylbenzamidine in the form of slightly red crystals; m.p. 71–73° C.

TABLE 6

Compounds of the general formula X (Xa and Xb)

E/Z-isomers

| Cmpd. no. | R₁ | R₂ | R₃ | R₆ | R₅ | phys. data m.p. ° C. |
|---|---|---|---|---|---|---|
| 6.1 | Cl | H | H | Me | Et | |
| 6.2 | Cl | H | H | Me | n-Propyl | 71–73 |
| 6.3 | Cl | H | H | Me | Allyl | 73–75 |
| 6.4 | Cl | H | H | Me | n-Butyl | oil; (¹H-NMR) |
| 6.5 | Cl | H | H | Me | i-Butyl | 86–89 |
| 6.6 | Cl | H | H | Me | CH₂-cyclopropyl | 108–110 |
| 6.7 | Cl | H | H | Me | n-Pentyl | |
| 6.8 | Br | H | H | Me | Et | |
| 6.9 | Br | H | H | Me | n-Propyl | oil |
| 6.10 | Br | H | H | Me | Allyl | |
| 6.11 | Br | H | H | Me | n-Butyl | |
| 6.12 | Br | H | H | Me | i-Butyl | |
| 6.13 | Br | H | H | Me | CH₂-cyclopropyl | |
| 6.14 | Br | H | H | Me | n-Pentyl | |
| 6.15 | F | H | H | Me | n-Propyl | |
| 6.16 | F | H | H | Me | n-Butyl | |
| 6.17 | H | Cl | H | Me | n-Propyl | oil |
| 6.18 | H | Cl | H | Me | Allyl | |
| 6.19 | H | Cl | H | Me | n-Butyl | |
| 6.20 | H | Br | H | Me | n-Propyl | |
| 6.21 | H | Br | H | Me | n-Butyl | |
| 6.22 | H | F | H | Me | n-Propyl | |
| 6.23 | H | I | H | Me | n-Butyl | |
| 6.24 | Br | H | Br | Me | Et | |
| 6.25 | Br | H | Br | Me | n-Propyl | oil |
| 6.26 | Br | H | Br | Me | Allyl | |
| 6.27 | Br | H | Br | Me | n-Butyl | |
| 6.28 | Br | H | Br | Me | i-Butyl | |
| 6.29 | Br | H | Br | Me | CH₂-cyclopropyl | |
| 6.30 | I | H | I | Me | Et | |
| 6.31 | I | H | I | Me | n-Propyl | |
| 6.32 | I | H | I | Me | Allyl | |
| 6.33 | I | H | I | Me | n-Butyl | |
| 6.34 | Cl | H | H | CF₃ | n-Propyl | |
| 6.35 | Cl | H | H | CF₃ | n-Butyl | |
| 6.36 | Br | H | H | CF₃ | n-Propyl | |
| 6.37 | Br | H | H | CF₃ | n-Butyl | |
| 6.38 | I | H | H | CF₃ | n-Propyl | |
| 6.39 | I | H | H | CF₃ | n-Butyl | |
| 6.40 | Cl | H | H | OMe | Et | |
| 6.41 | Cl | H | H | OMe | n-Propyl | 80-82 |
| 6.42 | Cl | H | H | OMe | Allyl | |
| 6.43 | Cl | H | H | OMe | n-Butyl | oil; (¹H-NMR) |
| 6.44 | Cl | H | H | OMe | i-Butyl | |
| 6.45 | Cl | H | H | OMe | CH₂-cyclopropyl | |

TABLE 6-continued

Compounds of the general formula X (Xa and Xb)

E/Z-isomers

| Cmpd. no. | R₁ | R₂ | R₃ | R₆ | R₅ | phys. data m.p. ° C. |
|---|---|---|---|---|---|---|
| 6.46 | Br | H | H | OMe | Et | |
| 6.47 | Br | H | H | OMe | n-Propyl | oil |
| 6.48 | Br | H | H | OMe | Allyl | |
| 6.49 | Br | H | H | OMe | n-Butyl | |
| 6.50 | Br | H | H | OMe | i-Butyl | |
| 6.51 | Br | H | H | OMe | CH₂—◁ | |
| 6.52 | I | H | H | OMe | Et | |
| 6.53 | I | H | H | OMe | n-Propyl | |
| 6.54 | I | H | H | OMe | Allyl | |
| 6.55 | I | H | H | OMe | n-Butyl | |
| 6.56 | I | H | H | OMe | i-Butyl | |
| 6.57 | H | Cl | H | OMe | n-Propyl | |
| 6.58 | H | Cl | H | OMe | Allyl | |
| 6.59 | H | Cl | H | OMe | n-Butyl | |
| 6.60 | Cl | H | Cl | OMe | n-Propyl | |
| 6.61 | Br | H | Br | OMe | Et | |
| 6.62 | Br | H | Br | OMe | n-Propyl | |
| 6.63 | Br | H | Br | OMe | Allyl | |
| 6.64 | Br | H | Br | OMe | n-Butyl | |
| 6.65 | Br | H | Br | OMe | i-Butyl | |
| 6.66 | I | H | I | OMe | n-Propyl | |
| 6.67 | I | H | I | OMe | Allyl | |
| 6.68 | I | H | I | OMe | n-Butyl | |
| 6.69 | I | H | I | OMe | i-Butyl | |
| 6.70 | Cl | H | H | OCF₃ | Et | |
| 6.71 | Cl | H | H | OCF₃ | n-Propyl | |
| 6.72 | Cl | H | H | OCF₃ | Allyl | |
| 6.73 | Cl | H | H | OCF₃ | n-Butyl | |
| 6.74 | Br | H | H | OCF₃ | n-Propyl | |
| 6.75 | Br | H | H | OCF₃ | Allyl | |
| 6.76 | Br | H | H | OCF₃ | n-Butyl | |
| 6.77 | I | H | H | OCF₃ | n-Propyl | |
| 6.78 | I | H | H | OCF₃ | n-Butyl | |
| 6.79 | Br | H | Br | OCF₃ | n-Propyl | |
| 6.80 | Br | H | Br | OCF₃ | n-Butyl | |
| 6.81 | I | H | I | OCF₃ | n-Propyl | |
| 6.82 | I | H | I | OCF₃ | n-Butyl | |

TABLE 7

¹H-NMR-data (ppm/multiplicity/number
Compound No. of H's); solvent: CDCl₃

| | |
|---|---|
| 6.4 | 0.89/t/3H; 1.31/m/2H; 1.50/m/2H; 2.82/s(broad)/3H; 3.10/m(broad)/2H; 7.36/d/1H; 7.52/dd/1H; 8.08/d/1H. |
| 6.43 | 0.86/t/3H; 1.32/m/2H; 1.45/m/2H; 2.86/q/2H; 3.80/s/3H 5.26/t/1H; 7.52–7.57/m/2H; 8.02/d/1H. |

Examples for specific formulations-combination are as disclosed e.g. in WO 97/33890, e.g. solutions and suspension concentrates.

BIOLOGICAL EXAMPLES

Fungicidal Actions

Example B-1

Action Against *Colletotrichum Lagenarium* on Cucumbers

After a growth period of 2 weeks, cucumber plants are sprayed with an aqueous spray mixture (concentration 0.002%) prepared from a wettable powder formulation of the test compound and infected 2 days later with a spore suspension ($1.5 \times 10^5$ spores/ml) of the fungus and incubated for 36 hours at 23° C. and high humidity. Incubation is then continued at normal humidity and c. 22° C. Evaluation of the fungal infestation is made 8 days after infection.

The compounds of the Tables 1–4 show good to excellent activity, preferably the compounds 1.72, 1.81, 1.152, 1.160, 2.11, 3.6, 4.3, 4.5, 4.6, 4.27, 4.29, 4.30, 4.36, 4.38, 4.39, 4.43, 4.45, 4.62, 4.80 and 4.111.

Example B-2

Residual-Protective Action Against *Venturia Inaegualis* on Apples

Apple cuttings with fresh shoots 10 to 20 cm long are sprayed to drip point with a spray mixture (0.02% a.i.) prepared from a wettable powder formulation of the test compound. The plants are infected 24 hours later with a conidia suspension of the fungus. The plants are then incubated for 5 days at 90 to 100% relative humidity and stood in a greenhouse for a further 10 days at 20 to 24° C. Evaluation of the fungal infestation is made 12 days after infection.

Compounds of Tables 1–4 show good activity, preferably the compounds 1.72, 1.81, 1.152, 1.160, 2.11, 3.6, 4.3, 4.5, 4.6, 4.27, 4.29, 4.30, 4.36, 4.38, 4.39, 4.43, 4.45, 4.62, 4.80 and 4.111.

Example B-3

Action Against *Erysiphe Graminis* on Barley a) Residual-Protective Action

Barley plants about 8 cm in height are sprayed to drip point with a spray mixture (0.02% a.i.) prepared from a wettable powder formulation of the test compound, and the treated plants are dusted with conidia of the fungus 3 to 4 hours later. The infected plants are stood in a greenhouse at 22° C. Evaluation of the fungal infection is made 12 days after infection.

b) Systemic Action

Barley plants about 8 cm in height are drenched with an aqueous spray mixture (0.002% a.i., based on the volume of the soil) prepared from a wettable powder formulation of the test compound. Care is taken that the spray mixture does not come into contact with the growing parts of the plants. The treated plants are dusted 48 hours later with conidia of the fungus. The infected plants are then stood in a greenhouse at 22° C. Evaluation of the fungal infestation is made 12 days after infection.

Compared with the control plants, infestation of the plants treated with compounds of formula I from Tables 1–4, for example the compounds 1.72, 1.81, 1.152, 1.160, 2.11, 3.6, 4.3, 4.5, 4.6, 4.27, 4.29, 4.30, 4.36, 4.38, 4.39, 4.43, 4.45, 4.62, 4.80 and 4.111 is 20% or less.

Example B-4

Action Against *Podosphaera Leucotricha* on Apple Shoots

Apple cuttings with fresh shoots about 15 cm long are sprayed with a spray mixture (0.06% a.i.). The plants are infected 24 hours later with a conidia suspension of the fungus and stood in a climatic chamber at 70% relative humidity and 20° C. Evaluation of the fugal infestation is made 12 days after infection.

Compounds of Tables 1–4 show good activity. The following compounds exhibit especially strong efficacy: 1.72, 1.81, 1.152, 1.160, 2.11, 3.6, 4.3, 4.5, 4.6, 4.27, 4.29, 4.30, 4.36, 4.38, 4.39, 4.43, 4.45, 4.62, 4.80 and 4.111 (0–5% infestation).

Example B-5

Action Against *Plasmopara Viticola* on Vines a) Residual-Preventive Action

Vine cuttings of the Chasselas variety are raised in a greenhouse. At the 10-leaf stage, 3 plants are sprayed with a spray mixture (200 ppm a.i.). After the spray coating has dried, the plants are infected uniformly on the underside of the leaves with a spore suspension of the fungus. The plants are then kept in a humidity chamber for 8 days, after which time marked symptoms of disease are observed on the control plants. The number and size of the infected areas on the untreated plants act as an indicator of the efficacy of the tested compounds.

b) Curative Action

Vine cuttings of the Chasselas variety are raised in a greenhouse and sprayed at the 10-leaf stage on the underside of the leaves with a spore suspension of *Plasmopara viticola*. After 24 hours in the humidity chamber, the plants are sprayed with a spray mixture (200 ppm a.i.). The plants are then kept for another 7 days in the humidity chamber. After this time the control plants exhibit symptoms of the disease. The number and size of the infected areas on the untreated plants act as an indicator of the efficacy of the tested compounds.

Compounds of Tables 1–4 show good efficacy.

Example B-6

Action Against *Uncinula Necator* on Vines 5 week old vine cuttings are sprayed with a spray mixture (200 ppm a.i.) prepared from a wettable powder formulation of the test compound. The plants are infected 24 hours later by conidias from strongly infested vine leafs that are shaken off over the test plants. The plants are then incubated at 26° C. and 60% relative humidity. The evaluation of the fungal infestation is made ca. 14 days after infection.

Compared with the control plants, infestation of the plants treated with compounds of formula I from the Tables 1–4, for example the compounds 1.72, 1.81, 1.152, 1.160, 2.11, 3.6, 4.3, 4.5, 4.6, 4.27, 4.29, 4.30, 4.36, 4.38, 4.39, 4.43, 4.45, 4.62, 4.80 and 4.111 is 20% or less.

Example B-7

Action Against *Aphis Craccivora*

Pea seedlings are infected with *Aphis craccivora*, subsequently sprayed with a spray liquor comprising 400 ppm of active compound I, and then incubated at 20° C. 3 and 6 days later, the percentage reduction in the population (% action) is determined by comparison of the number of dead aphids on the treated and on the untreated plants.

Compounds of the Tables 1–4 show a good action in this test, i.e. a destruction rate of more than 80%.

Example B-8

Action Against *Diabrotica Balteata*

Maize seedlings are sprayed with an aqueous emulsion spray liquor comprising 400 ppm of active compound I and, after the spray coating has dried on, are populated with 10 larvae of the second stage of *Diabrotica balteata* and then placed in plastic containers. 6 days later, the percentage reduction in the population (% action) is determined by comparison of the number of dead larvae between the treated and untreated plants.

Compounds of the Tables 1–4 show a good action in this test.

Example B-9

Action Against *Heliothis Virescens*

Young soya plants are sprayed with aqueous emulsion spray liquor comprising 400 ppm of active compound I and, after the spray coating has dried on, are populated with 10 caterpillars of the first stage of *Heliothis virescens* and then placed in plastic containers. 6 days later, the percentage reduction in the population and the feeding damage (% action) are determined by comparison of the number of dead caterpillars and of the feeding damage between treated and untreated plants.

Compounds of the Tables 1–4 show a good action in this test.

Example B-10

Action Against *Spodoptera Littoralis*

Young soya plants are sprayed with aqueous emulsion spray liquor comprising 400 ppm of active compound I and, after the spray coating has dried on, are populated with 10 caterpillars of the third stage of *Spodoptera littoralis* and then placed in plastic containers. 3 days later, the percentage reduction in the population and the percentage reduction in the feeding damage (% action) are determined by comparison of the number of dead caterpillars and of the feeding damage between the treated and untreated plants.

Compounds of the Tables 1–4 show a good action in this test.

Example B-11

Action Against *Nilaparvata Lugens*

Rice plants are treated with an aqueous emulsion spray liquor comprising 400 ppm of active compound I. After the spray coating has dried on, the rice plants are populated with cicada larvae of the 2nd and 3rd stage. The evaluation is carried out 21 days later. The percentage reduction in the population (% action) is determined by comparison of the number of surviving cicadas on the treated plants to those on the untreated plants.

The compounds of the Tables 1–4 show an action of more than 90%.

Example B-12

Action Against *Musca Domestica*

A sugar cube is treated with a solution of the test substance such that the concentration of test substance, after drying over night, in the sugar is 250 ppm. This treated cube is placed on an aluminium dish with a wet cotton-wool swab and 10 adult *Musca domestica* of an OP resistant strain, covered with a glass beaker and incubated at 25° C. After 24 hours, the mortality rate is determined.

Compounds from the Tables 1–4 show a good action.

Example B-13

Action Against *Tetranychus Urticae*

Young bean plants are populated with a mixed population of *Tetranychus urticae,* and one day later are sprayed with an aqueous emulsion spray liquor comprising 400 ppm of the active compound I. The plants are then incubated for 6 days at 25° C. and thereafter evaluated. The percentage reduction in the population (% action) is determined by comparison of the number of dead eggs, larvae and adults on the treated to those on the untreated plants.

Compounds of the Tables 1–4 show a good action.

What is claimed is:

1. A compound of formula I

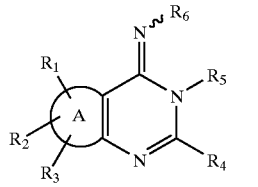

(I)

wherein

A is a 5- or 6-membered ring which may be saturated or unsaturated, aromatic or non-aromatic and which may contain no hetero atoms or 1–3 hetero atoms O, S and/or N, each in the free form or in salt form; with the exception of the imidazol ring;

$R_1$, $R_2$ and $R_3$ are each independently of the other hydrogen; halogen; $C_1$–$C_8$alkyl, $C_2$–$C_8$alkenyl or $C_2$–$C_8$alkinyl which are unsubstituted or mono- to tri-substituted by $C_3$–$C_6$cycloalkyl, halogen, $C_1$–$C_6$alkoxy, $C_1$–$C_6$alkylthio or $C_1$–$C_6$haloalkoxy; O—$C_1$–$C_6$alkyl, $C_2$–$C_6$alkenyl, O—$C_2$–$C_6$alkynyl, S—$C_1$–$C_6$alkyl, S—$C_2$–$C_6$alkenyl or S—$C_2$–$C_6$alkynyl, which are unsubstituted or mono- to tri-substituted by $C_3$–$C_6$cycloalkyl, halogen, $C_1$–$C_6$alkoxy or $C_1$–$C_6$haloalkoxy; cyano; nitro; or trimethylsilyl; provided that $R_1$, $R_2$ and $R_3$ are not hydrogen at the same time;

$R_4$ is $C_1$–$C_8$alkyl, $C_2$–$C_8$alkenyl or $C_2$–$C_8$alkinyl which are unsubstituted or mono- to tri-substituted by $C_3$–$C_6$cycloalkyl, halogen, cyano, nitro, CO—$C_1$–$C_4$alkyl, COO—$C_1$–$C_4$alkyl, CO-aryl, COO-aryl, $C_1$–$C_6$alkoxy, $C_1$–$C_6$alkylthio or $C_1$–$C_6$haloalkoxy; $C_3$–$C_6$cycloalkyl which is unsubstituted or mono- to tri-substituted by $C_1$–$C_8$alkyl, $C_1$–$C_6$haloalkyl, halogen, cyano, $C_1$–$C_6$alkoxy or $C_1$–$C_6$haloalkoxy; phenyl or benzyl, in which the phenyl group is unsubstituted or mono- to pentasubstituted by halogen, cyano, nitro, $C_1$–$C_8$alkyl, $C_2$–$C_8$alkenyl, $C_2$–$C_8$alkinyl, $C_1$–$C_6$alkoxy, $C_1$–$C_6$haloalkoxy or $C_1$–$C_8$haloalkyl; $NHR_7$; $SR_7$; or $CR_7$;

$R_5$ is $C_1$–$C_8$alkyl, $C_2$–$C_8$alkenyl or $C_2$–$C_8$alkinyl which are unsubstituted or mono- to tri-substituted by $C_3$–$C_6$cycloalkyl, halogen, cyano, nitro, CO—$C_1$–$C_4$alkyl, COO—$C_1$–$C_4$alkyl, CO-aryl, COO-aryl, $C_1$–$C_6$alkoxy, $C_1$–$C_6$alkylthio or $C_1$–$C_6$haloalkoxy; $C_3$–$C_6$cycloalkyl which is unsubstituted or mono- to tri-substituted by $C_1$–$C_6$alkyl, halogen, cyano, $C_1$–$C_6$alkoxy, $C_1$–$C_6$haloalkyl or $C_1$–$C_6$haloalkoxy;

$R_6$ is hydrogen; $C_1$–$C_8$alkyl, $C_2$–$C_8$alkenyl or $C_2$–$C_8$alkinyl which are unsubstituted or mono- to tri substituted by $C_3$–$C_6$cycloalkyl, halogen, cyano, nitro, CO—$C_1$–$C_4$alkyl, COO—$C_1$–$C_4$alkyl, CO-aryl, COO-aryl, $C_1$–$C_6$alkoxy, $C_1$–$C_6$alkylthio or $C_1$–$C_6$haloalkoxy; $C_3$–$C_6$cycloalkyl which is unsubstituted or mono- to tri-substituted by $C_1$–$C_6$alkyl, halogen, cyano, $C_1$–$C_6$alkoxy, $C_1$–$C_6$haloalkyl or $C_1$–$C_6$haloalkoxy; O—$C_1$–$C_6$alkyl, O—$C_2$–$C_6$alkenyl, O—$C_2$–$C_6$alkynyl, S—$C_1$–$C_6$alkyl, S—$C_2$–$C_6$alkenyl or S—$C_2$–$C_6$alkynyl, which are unsubstituted or mono- to tri-substituted by $C_3$–$C_6$cycloalkyl, halogen, cyano, $C_1$–$C_6$alkoxy or $C_1$–$C_6$haloalkoxy; aryl or heteroaryl which are unsubstituted or mono- to tri-substituted by halogen, cyano, nitro, $C_1$–$C_6$alkyl, $C_1$–$C_6$haloalkyl, $C_1$–$C_6$alkoxy or $C_1$–$C_6$haloalkoxy; CO-heteroaryl; CO—$C_1$–$C_6$alkyl; CO—$C_1$–$C_6$alkyl-O—$C_1$–$C_6$alkyl; CO—$C_1$–$C_6$haloalkyl; $SO_2$—$C_1$–$C_6$alkyl; $SO_2$-aryl; CO-phenyl or CO—$C_1$–$C_6$alkyl-O-phenyl in which phenyl is unsubstituted or mono- to tri-substituted by halogen, cyano, nitro, $C_1$–$C_6$alkyl, $C_1$–$C_6$haloalkyl, $C_1$–$C_6$alkoxy or $C_1$–$C_6$haloalkoxy; $COOR_8$ wherein $R_8$ is $C_1$–$C_8$alkyl, $C_2$–$C_8$alkenyl, $C_2$–$C_8$alkynyl, $C_3$–$C_4$cycloalkyl or phenyl which is unsubstituted or mono- to tri-substituted by halogen, cyano, nitro, $C_1$–$C_6$alkyl, $C_1$–$C_6$haloalkyl, $C_1$–$C_6$alkoxy or $C_1$–$C_6$haloalkoxy; cyano; nitro; or halogen; and $R_7$ is $C_1$–$C_8$alkyl, $C_2$–$C_8$alkenyl or $C_2$–$C_8$alkinyl which are unsubstituted or mono- to tri-substituted by $C_3$–$C_6$cycloalkyl, halogen, cyano, nitro, CO—$C_1$–$C_4$alkyl, COO—$C_1$–$C_4$alkyl, CO-aryl, COO-aryl, $C_1$–$C_6$alkoxy, $C_1$–$C_6$alkylthio or $C_1$–$C_6$haloalkoxy; $C_3$–$C_6$cycloalkyl which is unsubstituted or mono- to tri-substituted by $C_1$–$C_6$alkyl, $C_1$–$C_6$haloalkyl, halogen, cyano, $C_1$–$C_6$alkoxy or $C_1$–$C_6$haloalkoxy; phenyl or benzyl, in which the phenyl group is unsubstituted or mono- to pentasubstituted by halogen, cyano, nitro, $C_1$–$C_8$alkyl, $C_2$–$C_8$alkenyl, $C_2$–$C_8$alkinyl, $C_1$–$C_6$alkoxy, $C_1$–$C_6$haloalkoxy or $C_1$–$C_8$haloalkyl.

2. A compound of formula I according to claim 1, wherein A is phenyl, cyclohexyl, cyclopentyl, pyridyl, pyrimidinyl, thienyl[3,2-d], thienyl[2,3-d], thienyl[3,4-d], pyrazolyl, thiazolyl or furyl.

3. A compound of formula I according to claim 2, wherein A is phenyl;

$R_1$, $R_2$ and $R_3$ are each independently of the other hydrogen; halogen; $C_1$–$C_5$alkyl, $C_2$–$C_5$alkenyl or $C_2$–$C_5$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; provided that $R_1$, $R_2$ and $R_3$ are not all hydrogen at the same time; and at least one of $R_1$, $R_2$ and $R_3$ is halogen;

$R_4$ is $C_1$–$C_5$alkyl, $C_2$–$C_5$alkenyl or $C_2$–$C_5$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; $NHR_7$; or $OR_7$;

$R_5$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, COO$C_1$–$C_4$alkyl, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; CO—$C_1$–$C_4$alkyl; CO—$C_1$–$C_4$haloalkyl; SO$_2$—$C_1$–$C_4$alkyl; SO$_2$-phenyl; CO—$C_1$–$C_4$alkyl-O—$C_1$–$C_4$alkyl; CO—$C_1$–$C_4$alkyl-O-phenyl; COOR$_8$ wherein R$_8$ is $C_1$–$C_4$alkyl or phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; nitro; or chlorine; and $R_7$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl.

4. A compound of formula I according to claim 3, wherein $R_1$, $R_2$ and $R_3$ are each independently of the other hydrogen; chlorine or bromine; $C_1$–$C_4$alkyl, $C_2$–$C_4$alkenyl or $C_2$–$C_4$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl or O—$C_2$–$C_4$alkynyl, which are unsubstituted or mono- to tri-substituted by cyclopropyl or halogen; provided that $R_1$, $R_2$ and $R_3$ are not hydrogen at the same time; and at least one of $R_1$, $R_2$ and $R_3$ is chlorine or bromine;

$R_4$ is $C_1$–$C_4$ alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; NHR$_7$; or OR$_7$;

$R_5$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; or nitro; and $R_7$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl.

5. A compound of formula I according to claim 2, wherein

A is pyridinyl;

$R_1$ and $R_2$ are each independently of the other hydrogen; halogen; $C_1$–$C_5$alkyl, $C_2$–$C_5$alkenyl or $C_2$–$C_5$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; provided that $R_1$ and $R_2$ are not all hydrogen at the same time; and at least one of $R_1$ and $R_2$ is halogen;

$R_4$ is $C_1$–$C_5$alkyl, $C_2$–$C_5$alkenyl or $C_2$–$C_5$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; NHR$_7$; or OR$_7$;

$R_5$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, COO$C_1$–$C_4$alkyl, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; CO—$C_1$–$C_4$alkyl; CO—$C_1$–$C_4$haloalkyl; SO$_2$—$C_1$–$C_4$alkyl; SO$_2$-phenyl; CO—$C_1$–$C_4$alkyl-O—$C_1$–$C_4$alkyl; CO—$C_1$–$C_4$alkyl-O-phenyl; COOR$_8$ wherein R$_8$ is $C_1$–$C_4$alkyl or phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; nitro; or chlorine; and $R_7$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl.

6. A compound of formula I according to claim 5, wherein
$R_1$ and $R_2$ are each independently of the other hydrogen; chlorine or bromine; $C_1$–$C_4$alkyl, $C_2$–$C_4$alkenyl or $C_2$–$C_4$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl or O—$C_2$–$C_4$alkynyl, which are unsubstituted or mono- to tri-substituted by cyclopropyl or halogen; provided that $R_1$ and $R_2$ are not hydrogen at the same time; and at least one of $R_1$ and $R_2$ is chlorine or bromine;
$R_4$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; $NHR_7$; or $OR_7$;
$R_5$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;
$R_6$ is hydrogen; $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; or nitro; and
$R_7$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl.

7. A compound of formula I according to claim 2, wherein
A is thienyl[2,3-d];
$R_1$ and $R_2$ are each independently of the other hydrogen; halogen; $C_1$–$C_5$alkyl, $C_2$–$C_5$alkenyl or $C_2$–$C_5$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; provided that $R_1$ and $R_2$ are not all hydrogen at the same time; and at least one of $R_1$ and $R_2$ is halogen;
$R_4$ is $C_1$–$C_5$alkyl, $C_2$–$C_5$alkenyl or $C_2$–$C_5$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; $NHR_7$; or $OR_7$;
$R_5$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;
$R_6$ is hydrogen; $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $COOC_1$–$C_4$alkyl, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; CO—$C_1$–$C_4$alkyl; CO—$C_1$–$C_4$haloalkyl; $SO_2$—$C_1$–$C_4$alkyl; $SO_2$-phenyl; CO—$C_1$–$C_4$alkyl-O—$C_1$–$C_4$alkyl; CO—$C_1$–$C_4$alkyl-O-phenyl; $COOR_8$ wherein $R_8$ is $C_1$–$C_4$alkyl or phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; nitro; or chlorine; and
$R_7$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl.

8. A compound of formula I according to claim 7, wherein
$R_1$ and $R_2$ are each independently of the other hydrogen; chlorine or bromine; $C_1$–$C_4$alkyl, $C_2$–$C_4$alkenyl or $C_2$–$C_4$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl or O—$C_2$–$C_4$alkynyl, which are unsubstituted or mono- to tri-substituted by cyclopropyl or halogen; provided that $R_1$ and $R_2$ are not hydrogen at the same time; and at least one of $R_1$ and $R_2$ is chlorine or bromine;

$R_4$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; $NHR_7$; or $OR_7$;

$R_5$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; or nitro; and $R_7$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl.

9. A compound of formula I according to claim 2, wherein
A is thienyl[3,2-d];

$R_1$ and $R_2$ are each independently of the other hydrogen; halogen; $C_1$–$C_5$alkyl, $C_2$–$C_5$alkenyl or $C_2$–$C_5$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl, O—$C_2$–$C_4$alkynyl, S—C,–$C_4$alkyl, S—$C_2$–$C_4$alkenyl or S—$C_2$–$C_4$alkynyl, which are unsubstituted or mono- to tri-substituted by cyclopropyl or halogen; provided that $R_1$ and $R_2$ are not all hydrogen at the same time; and at least one of $R_1$ and $R_2$ is halogen;

$R_4$ is $C_1$–$C_5$alkyl, $C_2$–$C_5$alkenyl or $C_2$–$C_5$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; $NHR_7$; or $OR_7$;

$R_5$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $COOC_1$–$C_4$alkyl, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; CO—$C_1$–$C_4$alkyl; CO—$C_1$–$C_4$haloalkyl; $SO_2$—$C_1$–$C_4$alkyl; $SO_2$-phenyl; CO—$C_1$–$C_4$alkyl-O—$C_1$–$C_4$alkyl; CO—$C_1$–$C_4$alkyl-O-phenyl; $COOR_8$ wherein $R_8$ is $C_1$–$C_4$alkyl or phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; nitro; or chlorine; and $R_7$ is $C_1$–$C_5$alkyl, $C_2$–$C_5$alkenyl or $C_2$–$C_5$alkinyl which are unsubstituted or mono to tri-substituted by $C_3$–$C_4$cycloalkyl, halogen, $C_1$–$C_4$alkoxy, $C_1$–$C_4$alkylthio or $C_1$–$C_4$haloalkoxy; $C_3$–$C_4$cycloalkyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl.

10. A compound of formula I according to claim 9, wherein $R_1$ and $R_2$ are each independently of the other hydrogen; chlorine or bromine; $C_1$–$C_4$alkyl, $C_2$–$C_4$alkenyl or $C_2$–$C_4$alkinyl which are unsubstituted or mono- to tri-substituted by cyclopropyl, halogen, $C_1$–$C_4$alkoxy, $C_1$–$C_4$alkylthio or $C_1$–$C_4$haloalkoxy; O—$C_1$–$C_4$alkyl, O—$C_2$–$C_4$alkenyl or O—$C_2$–$C_4$alkynyl, which are unsubstituted or mono- to tri-substituted by cyclopropyl or halogen; provided that $R_1$ and $R_2$ are not hydrogen at the same time; and at least one of $R_1$ and $R_2$ is chlorine or bromine;

$R_4$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl or benzyl, in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl; $NHR_7$; or $OR_7$;

$R_5$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy;

$R_6$ is hydrogen; $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, halogen, $C_1$–$C_4$alkoxy, $C_1$–$C_4$haloalkyl or $C_1$–$C_4$haloalkoxy; O—$C_1$–$C_4$alkyl, O—$C_2$–$C_4$alkenyl, O—$C_2$–$C_4$alkynyl, S—$C_1$–$C_4$alkyl, S—$C_2$–$C_4$alkenyl or S—$C_2$–$C_4$alkynyl, which are unsubstituted or mono- to tri-substituted by cyclopropyl or halogen; phenyl which is unsubstituted or mono- to tri-substituted by halogen, $C_1$–$C_4$alkyl, $C_1$–$C_4$haloalkyl, $C_1$–$C_4$alkoxy or $C_1$–$C_4$haloalkoxy; cyano; or nitro; and $R_7$ is $C_1$–$C_4$alkyl, $C_2$–$C_4$alkenyl or $C_2$–$C_4$alkinyl which are unsubstituted or mono to tri-substituted by cyclopropyl, halogen, $C_1$–$C_4$alkoxy, $C_1$–$C_4$alkylthio or $C_1$–$C_4$haloalkoxy; cyclopropyl which is unsubstituted or mono- to tri-substituted by $C_1$–$C_4$alkyl, $C_1$–$C_4$haloalkyl, halogen, $C_1$–$C_4$alkoxy or $C_1$–$C_4$haloalkoxy; phenyl in which the phenyl group is unsubstituted or mono- to pentasubstituted by halogen, $C_1$–$C_4$alkyl, $C_2$–$C_4$alkenyl, $C_2$–$C_4$alkinyl, $C_1$–$C_4$alkoxy, $C_1$–$C_4$haloalkoxy or $C_1$–$C_4$haloalkyl.

11. A composition for controlling and preventing pests, wherein the active ingredient is a compound as claimed in claim 1 together with a suitable carrier.

12. A method of controlling or preventing infestation of cultivated plants by phytopathogenic microorganisms by application of a compound of formula I as claimed in claim 1 to plants, to parts thereof or to the locus thereof.

13. A method according to claim 12, wherein the phytopathogenic microorganism is a fungal organism.

14. A method for the preparation of a compound of formula I according to claim 1, which comprises a) reacting a compound of formula III, wherein A, $R_1$, $R_2$, $R_3$, $R_4$ and $R_5$ have the meanings stated for formula I

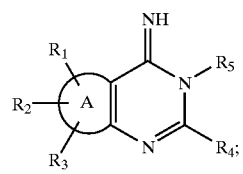

III with an electrophile $R_6X$ wherein $R_6$ has the meaning stated in claim 1 and X is a leaving group, to the compound of formula I; or b1) converting the compound of formula II to a compound of formula VII with a tetraalkylorthocarbonate $(COR_7)_4$ in the absence or presence of a catalyst in the presence or absence of a solvent

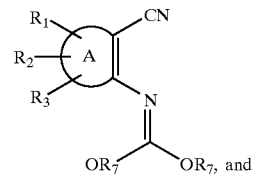

VII b2) converting the compound of formula VII to the compound of formula VIII with an amine $R_5NH_2$ under ring closure

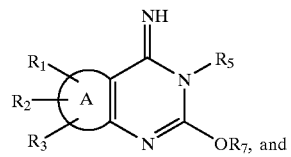

VIII b3) converting the compound VIII to the compound of formula I by reaction with an electrophile $R_6X$; or c1) converting the compound of formula II to the compound of formula VIII with $(RO_7)_2C=N—R_5$ and reacting the compound VIII with an electrophile $R_6X$; or d) reacting a compound of formula XI

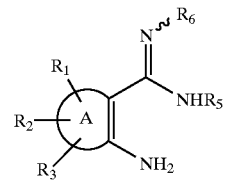

(XI)

with an orthocarbonate $C(OR_7)_4$ or an orthoester alkyl-$C(OR_7)_3$ wherein A, $R_1$, $R_1$, $R_3$, $R_4$, $R_5$, $R_6$ and $R_7$ have the meaning given in claim 1.

15. A compound of formula VI

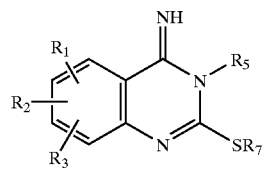

VI wherein $R_1$, $R_2$, $R_3$, $R_5$ and $R_7$ have the meaning given in claim 1.

* * * * *